(12) United States Patent
Kuwahata et al.

(10) Patent No.: US 11,353,525 B2
(45) Date of Patent: Jun. 7, 2022

(54) MAGNETIC BODY DETECTING DEVICE

(71) Applicant: MATRIX CELL RESEARCH INSTITUTE INC., Ushiku (JP)

(72) Inventors: Akihiro Kuwahata, Tokyo (JP); Moriaki Kusakabe, Ushiku (JP); Masaki Sekino, Tokyo (JP)

(73) Assignee: MATRIX CELL RESEARCH INSTITUTE INC., Ushiku (JP)

( * ) Notice: Subject to any disclaimer, the term of this patent is extended or adjusted under 35 U.S.C. 154(b) by 32 days.

(21) Appl. No.: 17/257,232

(22) PCT Filed: Jul. 8, 2019

(86) PCT No.: PCT/JP2019/026970
§ 371 (c)(1),
(2) Date: Dec. 30, 2020

(87) PCT Pub. No.: WO2020/013123
PCT Pub. Date: Jan. 16, 2020

(65) Prior Publication Data
US 2021/0123989 A1    Apr. 29, 2021

(30) Foreign Application Priority Data

Jul. 8, 2018 (JP) .............................. JP2018-129567

(51) Int. Cl.
*G01R 33/07* (2006.01)
*G01R 33/00* (2006.01)
*G01R 33/022* (2006.01)

(52) U.S. Cl.
CPC ......... *G01R 33/07* (2013.01); *G01R 33/0047* (2013.01); *G01R 33/022* (2013.01)

(58) Field of Classification Search
CPC ................ G01R 33/00; G01R 33/0035; G01R 33/0023; G01R 33/0017; G01R 31/3191;
(Continued)

(56) References Cited

U.S. PATENT DOCUMENTS

2002/0101233 A1*  8/2002  Yokotani ............... G01D 5/147
                                                          324/207.21
2004/0162477 A1   8/2004  Okamura et al.
(Continued)

FOREIGN PATENT DOCUMENTS

EP    3 309 570 A1    4/2018
JP    2002-228733 A   8/2002
(Continued)

OTHER PUBLICATIONS

Sep. 3, 2019 International Search Report issued in International Patent Application No. PCT/JP2019/026970.
(Continued)

*Primary Examiner* — Jermele M Hollington
*Assistant Examiner* — Taqi R Nasir
(74) *Attorney, Agent, or Firm* — Oliff PLC

(57) ABSTRACT

A magnetic body detecting device constituting a magnet portion for magnetizing a magnetic body from a magnet main body portion, and a correcting portion which is disposed in front of magnet main body portion to correct a magnetic field generated by magnet main body portion, wherein the correcting portion is configured to form a specific position N having a desired magnetic field intensity by canceling out the magnetic field generated by magnet main body portion, and to adjust the magnetic field gradient at a magnetic field null point N of the magnetic field generated by magnet portion by causing magnet main body portion to be separated from a front end portion of magnet portion in accordance with the magnetic field gradient in the correcting portion, and wherein a magnetic sensor is disposed at the magnetic field null point N formed in the front end portion of the magnet portion.

9 Claims, 16 Drawing Sheets

(58) Field of Classification Search
CPC .. G01R 33/07; G01R 33/0047; G01R 33/022; G01B 7/004; G01C 17/38; G06F 3/017; G06F 3/0346; G06F 3/012
See application file for complete search history.

(56) References Cited

U.S. PATENT DOCUMENTS

| | | | |
|---|---|---|---|
| 2015/0260805 A1* | 9/2015 | Miura | G01R 33/1253 324/228 |
| 2017/0234699 A1 | 8/2017 | Ausserlechner | |
| 2017/0261565 A1* | 9/2017 | Ausserlechner | G01R 33/0017 |
| 2018/0242877 A1* | 8/2018 | Kusakabe | A61B 5/418 |

FOREIGN PATENT DOCUMENTS

| | | |
|---|---|---|
| JP | 3847694 B2 | 11/2006 |
| JP | 3960558 B1 | 8/2007 |
| JP | 2013-169382 A | 9/2013 |
| JP | 2015-175647 A | 10/2015 |
| JP | 2017-003394 A | 1/2017 |
| JP | 2018-050874 A | 4/2018 |
| WO | 2017/081783 A1 | 5/2017 |

OTHER PUBLICATIONS

Jan. 12, 2021 International Preliminary Report on Patentability issued in International Patent Application No. PCT/JP2019/026970.

\* cited by examiner

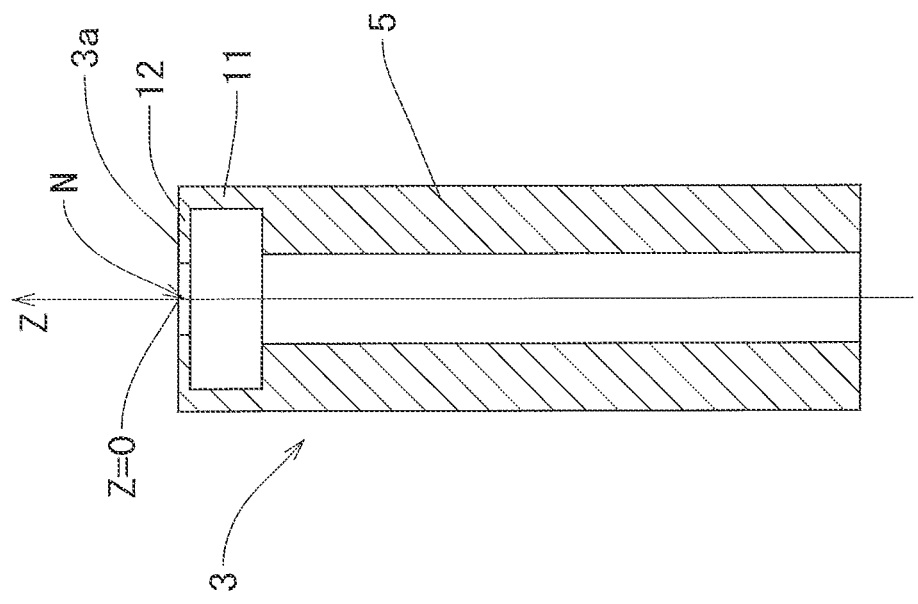
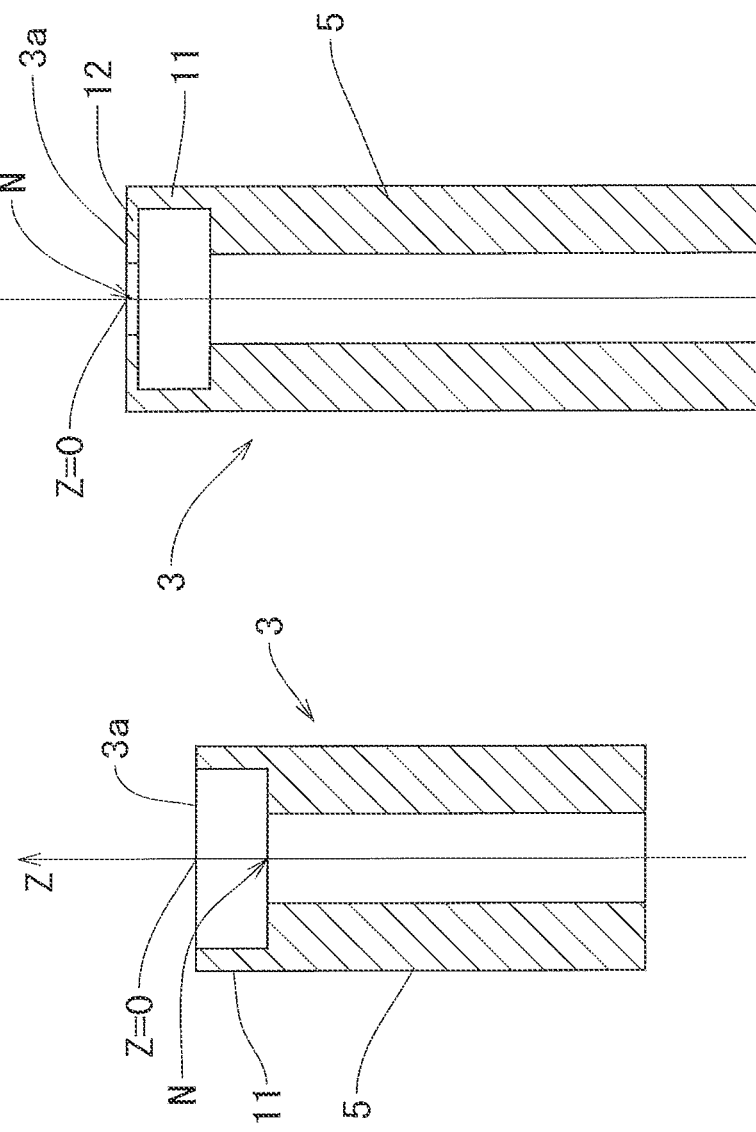
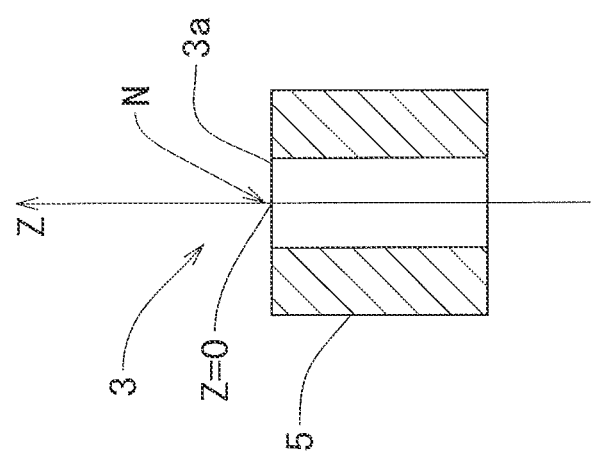

Temp₀=25°C  B₀=-1mT

Temp₀=25°C  B₀=0mT

Temp₀=25°C  B₀=1mT

Temp₀=25°C  B₀=2mT

Temp₀=36.3°C B₀=-1mT

Temp₀=36.3°C B₀=0mT

Temp₀=36.3°C B₀=1mT

Temp₀=36.3°C B₀=2mT

MAGNETIC BODY DETECTING DEVICE

TECHNICAL FIELD

The present invention relates to a magnetic body detecting device to be used for detecting a magnetic body.

BACKGROUND ART

It is conventional practice to check and specify a state of a living body by injecting a magnetic body into the living body and detecting the magnetism of the magnetic body at a specific part or tissue. For example, in treatment of breast cancer, biopsy of a sentinel lymph node is performed to check for metastasis of cancer cells. In this process, it must be specified which lymph node among extracted lymph nodes is the sentinel lymph node. As a method for specifying the sentinel lymph node, there is known that which is performed by injecting a magnetic fluid into a lesion site and detecting the magnetism of the injected magnetic fluid after elapse of an appropriate time.

As magnetic body detecting devices that detect the magnetism from such a magnetic body inside a living body, there are known devices such as those described, for example, in Patent Literatures 1 and 2 that are compact and use a permanent magnet to magnetize the magnetic body. Such magnetic body detecting devices have a magnetic sensor disposed at a tip central portion of a permanent magnet of circular cylindrical shape and are arranged such that the magnetic body is magnetized by an excitation magnetic field due to the permanent magnet to detect the magnetism of the magnetic body by the magnetic sensor. Also, the magnetic sensor is disposed in a region (magnetic field null point) in which the magnetic field generated by the permanent magnet is not detected when a magnetic body is not present nearby.

Also, generally in such magnetic body detecting devices, a magnetic sensor is also disposed at a rear of the permanent magnet. As this rear magnetic sensor, that which is the same as the magnetic sensor at the tip side is disposed in the same direction and detects geomagnetism. By then performing correction in the manner of subtracting a detection value of the magnetic sensor at the rear from a detection value of the magnetic sensor at the tip side, influence due to geomagnetism is eliminated.

CITATION LIST

Patent Literatures

Patent Literature 1: Japanese Patent No. 3960558
Patent Literature 2: International Publication No. WO 2017/081783

SUMMARY OF INVENTION

Technical Problem

Incidentally, the permanent magnet of simple circular cylindrical shape adopted in the magnetic body detecting devices described above has a problem in that although the magnetic field null point is formed in a vicinity of the tip of the permanent magnet, a magnetic field gradient at that position is large. If the magnetic field gradient is large at the magnetic field null point, then, even when the magnetic sensor deviates at the micrometer level with respect to the permanent magnet, for example, due to the magnetic sensor and the permanent magnet undergoing temperature change such that thermal expansion or thermal contraction occurs, etc., this may have a large influence and deviation from a desired magnetic field strength may occur. If the magnetic sensor is separated from an end portion of the permanent magnet, the magnetic field gradient decreases gradually and therefore, with the magnetic sensor for detecting geomagnetism, by separating further rearward than a rear end portion of the permanent magnet, both the magnetic field strength and the magnetic field gradient can be reduced in influence by the permanent magnet. On the other hand, if the magnetic sensor at the tip side is separated from the tip portion of the permanent magnet, a magnetic body of a detection subject is also separated from the permanent magnet and therefore, detection is hindered. The conventional magnetic body detecting device is thus extremely sensitive in regard to disposition of the magnetic sensor and is easily influenced by deviation of the magnetic sensor. Therefore, a Hall element that is somewhat poor in sensitivity is used as the magnetic sensor and it was not possible to use a highly sensitive magnetic sensor such as an MI element, a GMR sensor, a GSR sensor, or a diamond sensor. Providing of a magnetic body detecting device that is reduced in magnetic field gradient at a disposed position of a magnetic sensor and capable of detection of high sensitivity is thus desired.

Solution to Problem

The present invention has been made in earnest to solve the above problem and the invention according to claim 1 is a magnetic body detecting device including a detecting portion at a front end that, in a state of being in contact with or proximity to a subject, detects a magnetic body and is a magnetic body detecting device wherein the detecting portion includes a magnet portion for magnetizing the magnetic body and a magnetic sensor for detecting magnetism, the magnet portion includes a magnet main body portion that is a permanent magnet and a correcting portion disposed at least at one of either a front or a rear of the magnet main body portion and correcting a magnetic field generated from the magnet main body portion and forms a specific position being a desired magnetic field strength in a vicinity of a front or rear end portion of the correcting portion, the correcting portion is arranged such as to cancel out the magnetic field generated by the magnet main body portion at a front or rear end portion of the magnet portion and adjust a magnetic field gradient of a magnetic field generated by the magnet portion at the specific position by performing separation inwardly in a front/rear direction from the front or rear end portion at which the correcting portion of the magnet main body portion is disposed in accordance with the magnetic field gradient of a magnetic field generated by the correcting portion, and the magnetic sensor is disposed at the specific position at which the magnetic field gradient is adjusted by the correcting portion.

The invention according to claim 2 is the magnetic body detecting device wherein the correcting portion is constituted of a first correcting portion disposed at an outer side in the front/rear direction with respect to the magnet main body portion and a second correcting portion constituted of a permanent magnet disposed at an outer side in the front/rear direction with respect to the first correcting portion, the first correcting portion adjusts a magnetic field gradient of the magnetic field generated by the magnet main body portion at the specific position by separating the magnet main body portion inwardly in the front/rear direction from the front or rear end portion of the magnet portion, and the second correcting portion adjusts a magnetic field gradient at the specific position by canceling out a magnetic field at the front or rear end portion of the magnet portion generated by the magnet portion excluding the second correcting portion.

The invention according to claim 3 is the magnetic body detecting device according to claim 2 wherein the specific position is formed by matching a peak of the magnetic field generated by the magnet portion excluding the second correcting portion and a peak of the magnetic field generated by the second correcting portion.

The invention according to claim 4 is the magnetic body detecting device according to claim 2 wherein the specific position is a magnetic field null point of the desired magnetic field strength of substantially 0 and the magnetic field null point is formed by matching a peak, being of one of either a positive or negative sign, of the magnetic field generated by the magnet portion excluding the second correcting portion and a peak, being of the other of the positive or negative sign, of the magnetic field generated by the second correcting portion.

The invention according to claim 5 is the magnetic body detecting device according to any one of claims 1 to 4 wherein the second correcting portion is shorter in front/rear length than the first correcting portion.

The invention according to claim 6 is the magnetic body detecting device according to any one of claims 1 to 5 wherein the first correcting portion is a permanent magnet of circular cylindrical shape with an inner diameter larger than an inner diameter of the magnet main body portion and the second correcting portion has a circular cylindrical shape with an inner diameter smaller than an inner diameter of the first correcting portion such that a hollow portion is formed in an interior of the correcting portion.

The invention according to claim 7 is the magnetic body detecting device according to any one of claims 1 to 6 wherein the desired magnetic field strength at the specific position is a magnetic field strength set based on a change amount of a detection value of the magnetic sensor accompanying a temperature change.

The invention according to claim 8 is the magnetic body detecting device according to any one of claims 1 to 7 wherein the magnetic sensor is disposed at the front end portion of the magnet portion and detects the magnetism of the magnetic body magnetized by the magnet portion.

The invention according to claim 9 is the magnetic body detecting device according to any one of claims 1 to 7 wherein the magnetic sensor is a geomagnetic sensor disposed at the rear end portion of the magnet portion and detects geomagnetism.

Advantageous Effects of Invention

By the inventions of claims 1 and 2, it is made possible to adjust and reduce the magnetic field gradient at the specific position being of the desired magnetic field strength by the correcting portion and therefore, even if the magnetic sensor and the magnet portion deviate due to thermal expansion, etc., occurring due to temperature change, highly sensitive detection with influence of the above being reducible is enabled.

By the invention of claim 3, the magnetic field gradient at the specific position can be made substantially 0.

By the invention of claim 4, the magnetic field null point with the magnetic field gradient being made substantially 0 can be formed easily.

By the invention of claim 5, the specific position can be disposed as much in front as possible while reducing the magnetic field gradient.

By the invention of claim 6, reduction of the magnetic field gradient at the specific position is enabled by processing of a single magnet material.

By the invention of claim 7, a detection result that is reduced in influence by temperature characteristics of the magnetic sensor can be obtained and therefore, highly sensitive detection is enabled.

By the invention of claim 8, the magnetic sensor that detects the magnetism of the detection subject is disposed at the specific position and therefore, highly sensitive detection is enabled.

By the invention of claim 9, the magnetic sensor that detects geomagnetism is disposed at the specific position and therefore, highly sensitive detection of geomagnetism is enabled while reducing influence by the magnet portion and the device can be made compact because the geomagnetic sensor can be housed within the magnet portion.

BRIEF DESCRIPTION OF DRAWINGS

FIG. 6 shows front sectional views of magnet portions having (A) just a magnet main body portion, (B) just the magnet main body portion and a first correcting portion, and (C) the magnet main body portion and first and second correcting portions.

DESCRIPTION OF EMBODIMENTS

Figure 1:
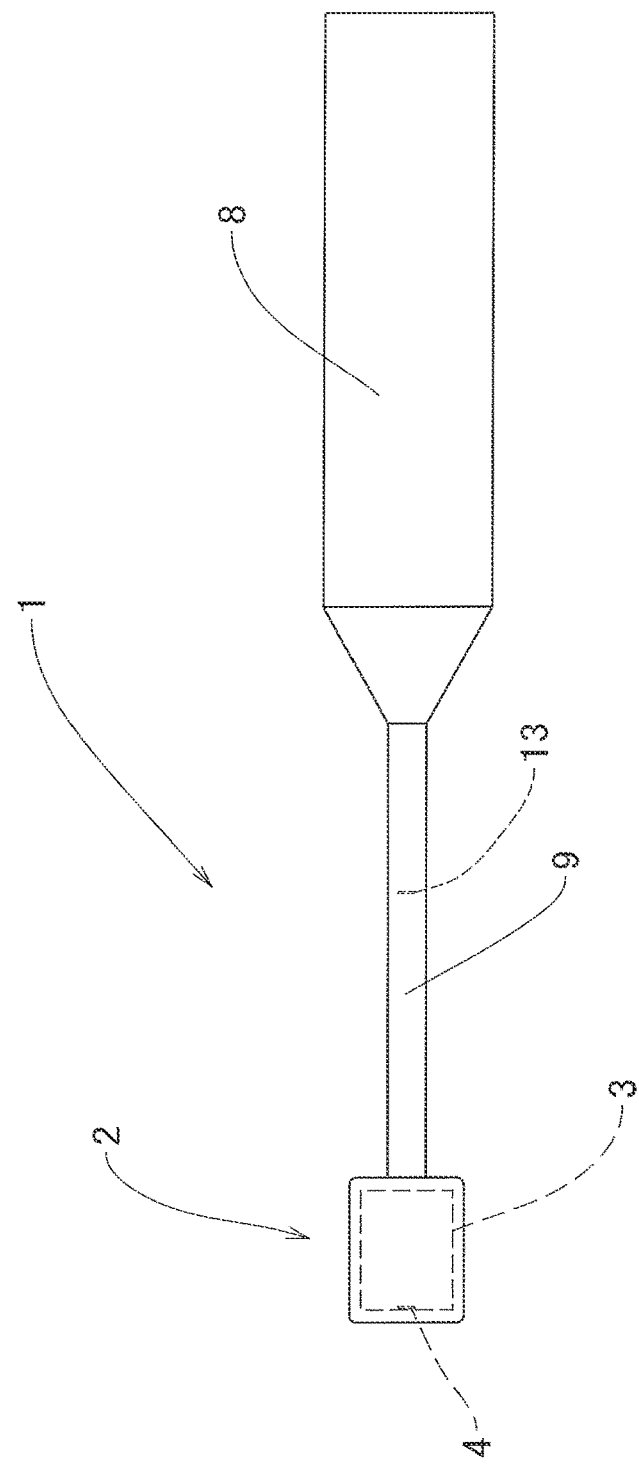
FIG. 1 is an overall view of a magnetic body detecting device according to a first embodiment.
Figure 2:
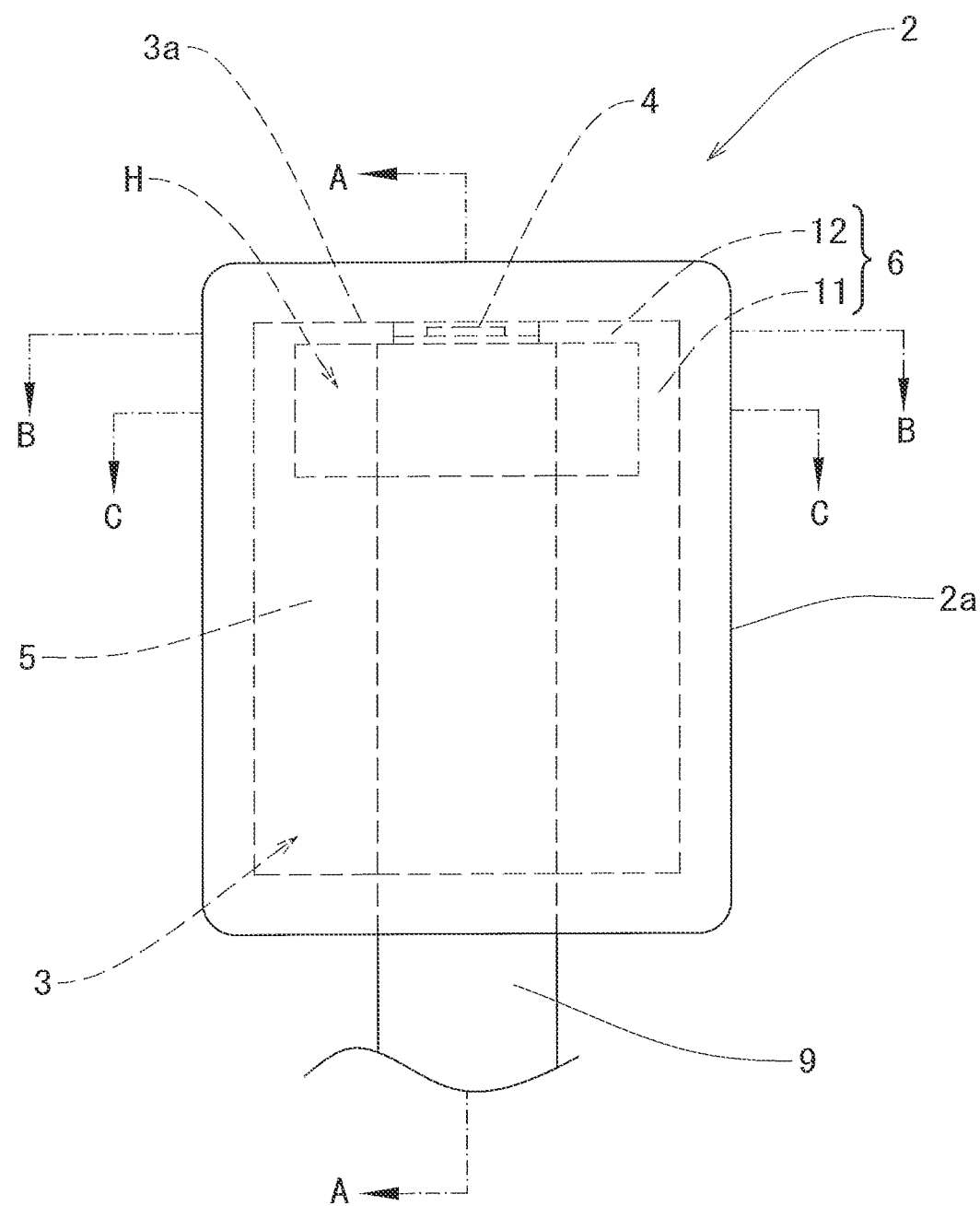
FIG. 2 is an enlarged view of a detecting portion.
Figure 3:
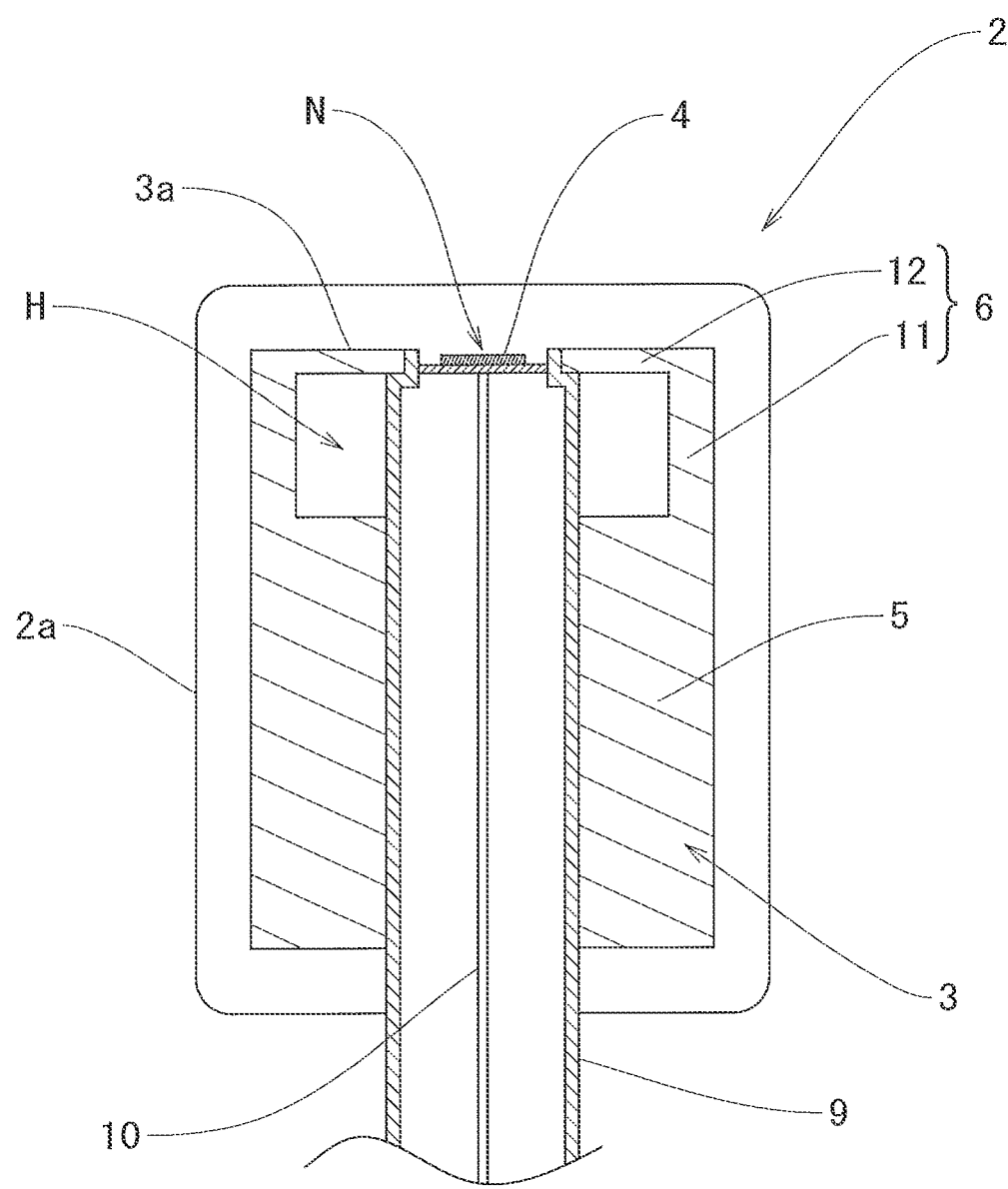
FIG. 3 is a sectional view taken along A-A of FIG. 2.
Figure 4A:
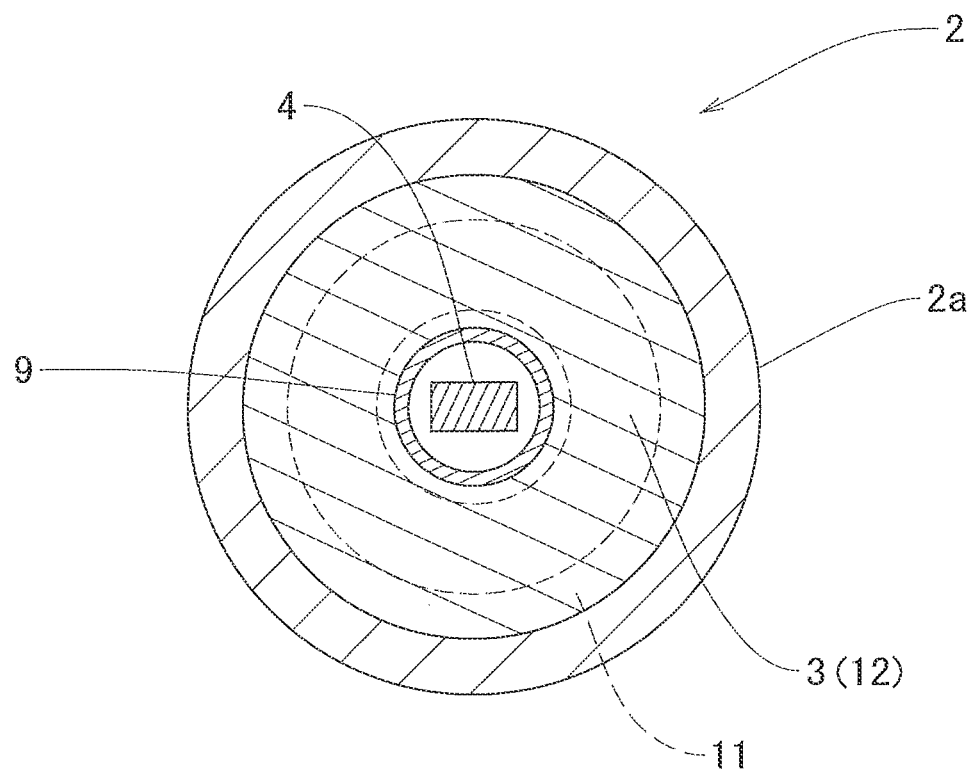
FIG. 4A is a sectional view taken along B-B of FIG. 2
Figure 4B:
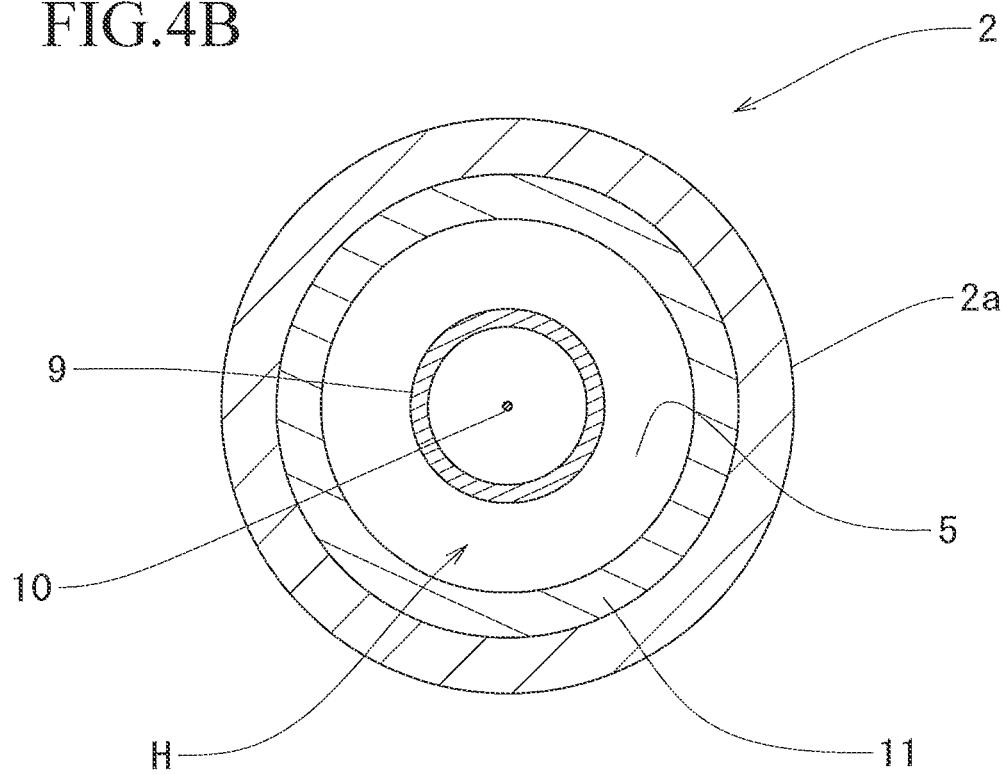
FIG. 4B is a sectional view taken along B-B of FIG. 2.
Figure 5A:
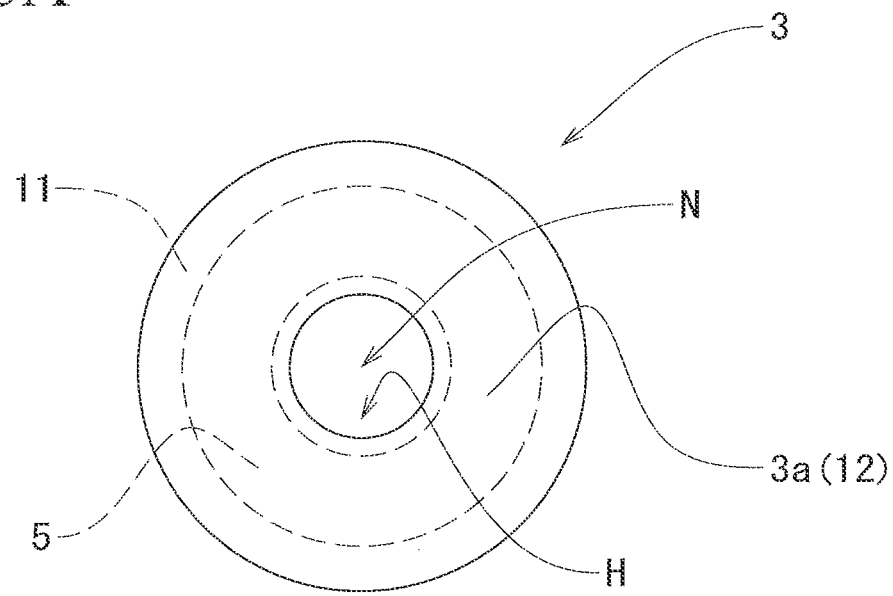
FIG. 5A is a plan view and FIG. 5B is a front view of a magnet portion.
Figure 5B:
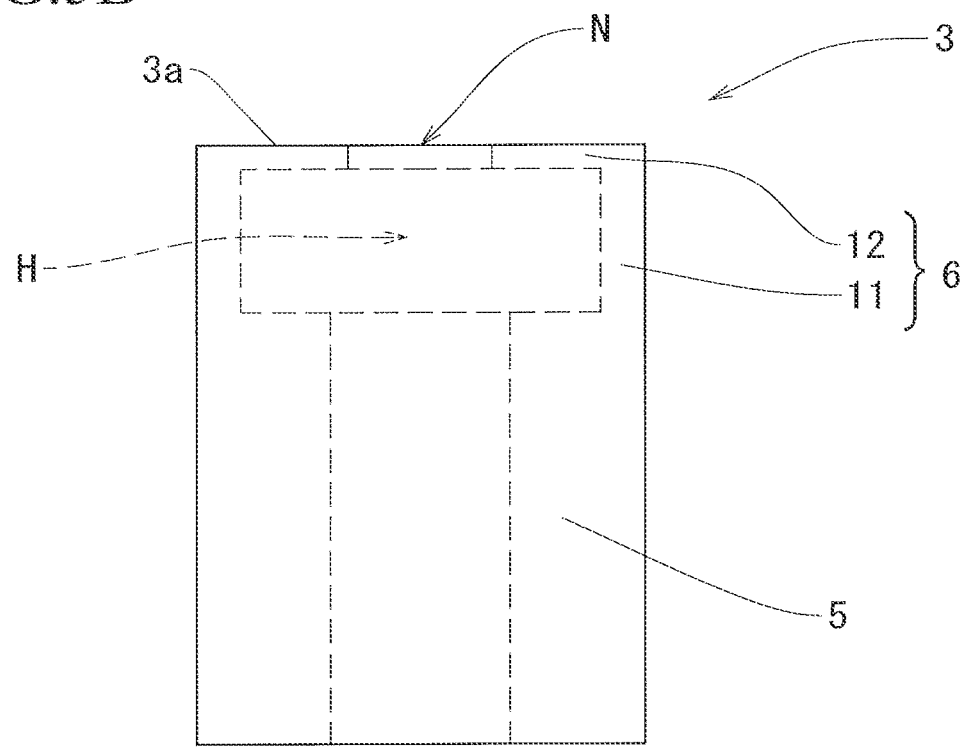

A first embodiment of the present invention shall be described with reference to the drawings. Reference numeral 1 denotes a magnetic body detecting device that detects a magnetic body. The magnetic body detecting device 1 includes a detecting portion 2 at a front side (tip side) that, in a state of being in contact with or proximity to a subject, detects the magnetic body. The detecting portion 2 includes a magnet portion 3 for magnetizing the magnetic body inside the subject and a first magnetic sensor 4 as a magnetic sensor for detecting magnetism of the magnetized magnetic body. The magnet portion 3 includes a magnet main body portion 5 that is a permanent magnet and a correcting portion 6 disposed at a front side (tip side) of the magnet main body portion 5. Here, the magnet portion 3 is arranged to form, at a front end portion 3a provided with the correcting portion 6, a magnetic field null point N that is a specific position being of a desired magnetic field strength. The magnetic field null point N is a region in which a magnetic field strength is substantially is zero when a magnetic body is not present nearby and changes in magnetic field strength in accordance with approach of the magnetic body. That is, the desired magnetic field strength in the present embodiment can be said to be substantially zero. Also, the correcting portion 6 has a shape with which a hollow portion H is formed in an interior. As shall be described below, by this correcting portion 6, a magnetic field gradient at the magnetic field null point N is adjusted and reduced and, in particular, a magnetic field generated from the magnet main body portion 5 is corrected such that the magnetic field gradient at the magnetic field null point N is substantially 0. Also, as shall be described below, the first magnetic sensor 4 is disposed at the magnetic field null point N at which the magnetic field gradient is made substantially 0 by the magnetic field gradient being adjusted by the correcting portion 6. A magnitude of a magnetic field gradient shall be referred to as being smaller the closer it is to zero (that is, shall mean a magnitude of an absolute value of the magnetic field gradient) and to reduce the magnetic field gradient shall refer to making the magnetic field gradient close to 0 (that is, to reduce the absolute value of the magnetic field gradient).

The magnetic body detecting device 1 further includes a case portion 8 at a rear portion. The detecting portion 2 and the case portion 8 are coupled by a shaft 9. An unillustrated controller, power supply portion, and outputting portion, etc., are housed in an interior of the case portion 8. The controller controls the outputting portion based on a detection value, etc., from the detecting portion 2. The power supply portion supplies power to the detecting portion 2, the controller, and the outputting portion, etc., with a battery, etc., as a power supply. The outputting portion outputs a detection result by a predetermined display, transmission by sound or data, etc., based on a signal from the detecting portion 2. Dispositions of these in the case portion 8 can be arranged as appropriate. Also, an external power supply may be used as the power supply. The shaft 9 is constituted of a nonmagnetic body of hollow shape that is elongate in a front/rear direction and a wiring cord 10 connecting the detecting portion 2 and the controller is inserted through its interior. Also, the shaft 9 may be arranged as one that is straight as shown in FIG. 1 or may have a shape, for example, that is bent in a vicinity of the detecting portion 2.

The magnet portion 3 and the first magnetic sensor 4 at a central portion of the front end portion 3a of the magnet portion 3 are disposed in an interior of the detecting portion 2. Also, the shaft 9 penetrates through an interior of the magnet portion 3, a front end portion of the shaft 9 is made a shape capable of fitting to a front end portion of the hollow portion H of the magnet portion 3 to be described below, and the first magnetic sensor 4 is disposed at a front end surface of the shaft 9. On the other hand, an outer periphery of the detecting portion 2 is covered by a cover body 2a constituted of a nonmagnetic body. By making the cover body 2a a heat insulating member formed, for example, of a resin material of low thermal conductivity, temperature change of the first magnetic sensor 4 and the magnet portion 3 can be suppressed. Furthermore, inside the detecting portion 2, a temperature sensor may be disposed in a vicinity of the first magnetic sensor 4 and further, a thermally conductive member may be disposed between the first magnetic sensor 4 and the temperature sensor. By disposing the temperature sensor, the detection result can be arranged to be output upon influence due to temperature being corrected for at the controller or the outputting portion.

The magnet portion 3 is a permanent magnet of circular cylindrical shape that differs in polarity at front and rear in an axial direction and is disposed inside the detecting portion 2 with an N pole side being at the front and an S pole side being at the rear. A direction of the magnetic poles may be such that the S pole side is at the rear and the N pole side is at the rear and is preferably matched with a polarity of the magnetic sensor. As the magnet portion 3, for example, a rare earth magnet such as neodymium magnet or a samarium cobalt magnet, etc., can be used. Also, a rear half portion of the magnet portion 3 is the magnet main body portion 5 of circular cylindrical shape. The magnet main body portion 5 is hollow in its interior and arranged such that the shaft 9 including the wiring cord 10 is insertable therethrough.

The correcting portion 6 disposed in front of the magnet main body portion 5 has a first correcting portion 11 at a rear side (magnet main body portion 5 side) and a second correcting portion 12 at a front side (first magnetic sensor 4 side). The first correcting portion 11 has a circular cylindrical shape that is hollow with an outer diameter being equal to that of the magnet main body portion 5 and an inner diameter being larger than that of the magnet main body portion 5. The second correcting portion 12 has a circular cylindrical shape that is hollow with an outer diameter being equal to that of the magnet main body portion 5 and an inner diameter smaller than that of the magnet main body portion 5 (and the first correcting portion 11). By the hollow shapes of the first correcting portion 11 and the second correcting portion 12, the hollow portion H is formed in the interior of the correcting portion 6. The hollow portion H has a shape that widens from the front to rear.

The magnet portion 3 that includes the correcting portion 6 forms the magnetic field null point N at which the magnetic field strength and the magnetic field gradient are substantially 0 in the front end portion 3a, and respective dispositions and shapes of the magnet main body portion 5, the first correcting portion 11, and the second correcting portion 12 in this case are arranged as follows.

Figure 7X:
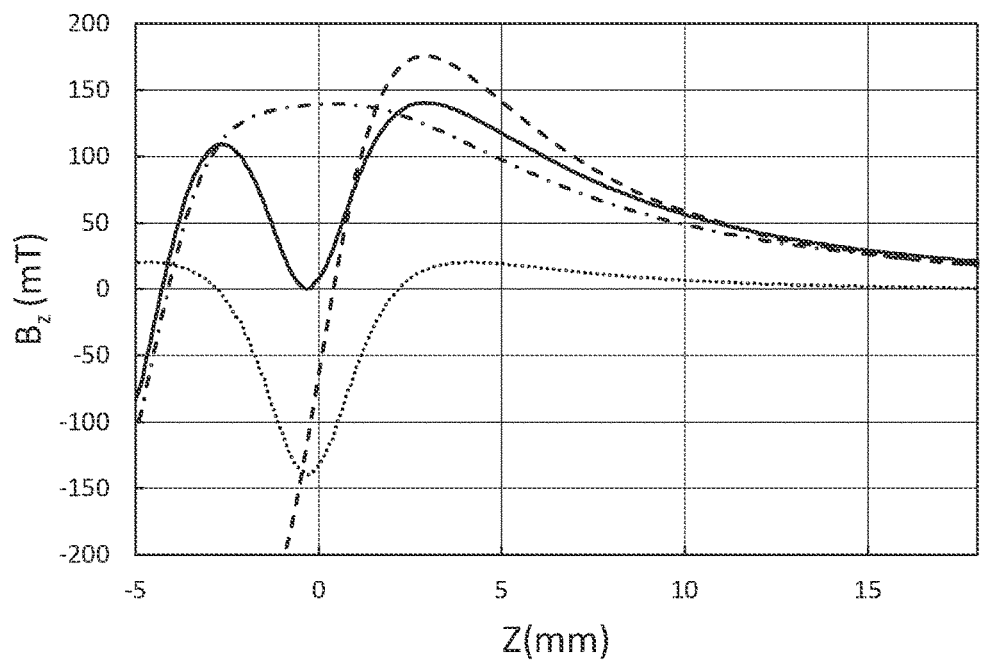
FIG. 7X is a graph showing a magnetic field and FIG. 7Y is a graph showing a change amount of the magnetic field (magnetic field gradient) in an axial direction (Z direction) of the magnet portion.
Figure 7Y:
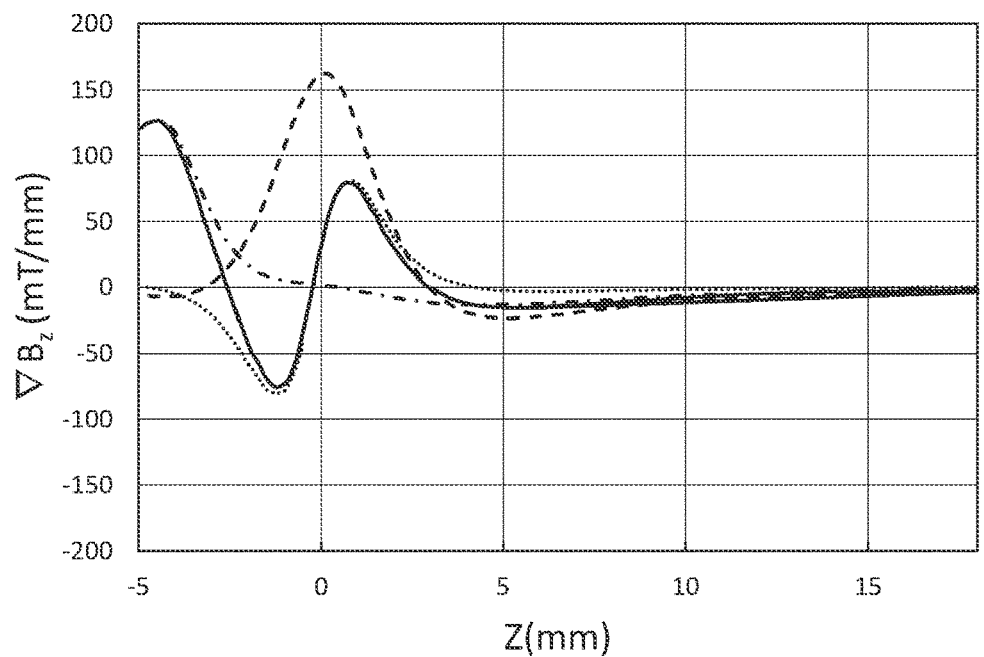

FIG. 6 shows structures of the magnet portion 3 in (A) a case where it is just the magnet main body portion 5, (B) a case where it is constituted of the magnet main body portion 5 and the first correcting portion 11, and (C) a case where it is constituted of the magnet main body portion 5 and the first and second correcting portions 11 and 12 (hereinafter referred to as "case of (A)," etc.). Then, with the axial direction being a Z axis direction, a forward direction being a positive direction, and a front end of the magnet portion 3 being set to be at Z=0, FIG. 7X shows the respective magnetic field strengths and FIG. 7Y shows change amounts of the magnetic field strengths, that is, the magnetic field gradients along the Z axis for (A) to (C) above in the form of graphs.

Specific numerical values at respective portions of the magnet portion 3 for obtaining the respective graphs of FIG. 7 are indicated below. An outer diameter of the magnet portion 3 is set to approximately 12.5 mm in all cases. The inner diameters of the magnet main body portion 5, the first correcting portion 11, and the second correcting portion 12 are set respectively to approximately 5.0 mm, 10.0 mm, and 4.0 mm. A front/rear length of the magnet portion 3 is set to approximately 12 mm, 21 mm, and 38 mm in the cases of (A), (B), and (C), respectively. Front/rear lengths of the first correcting portion 11 and the second correcting portion 12 are set to 4.0 mm and 0.66 mm, respectively. A front/rear length of the magnet main body portion 5 is a length obtained by subtracting the front/rear lengths of the first correcting portion 11 and the second correcting portion 12 from the front/rear length of the magnet portion 3 in each case. As the magnet portion 3, a neodymium magnet with a holding force of approximately 950 to 1000 kA/m and a residual magnetic flux density of approximately 1.3 T. However, the numerical values above are merely those of one example and the respective portions of appropriate size and strength can be adopted in accordance with a measurement subject, design, etc.

First, the case of (A) is that where the magnet portion 3 that is a permanent magnet of simple, circular cylindrical shape is disposed and this can be regard as being equivalent to a permanent magnet used in a conventional magnetic body detecting device. As is clear from the respective graphs of FIG. 7, in the case of (A), the magnetic field null point (region of magnetic field strength $B_z \approx 0$ mT) N is positioned at $Z \approx 0.3$ mm and the magnetic field gradient at this magnetic field null point N is such that $\nabla B_z \approx 150$ mT/mm. Therefore, in this case, the magnetic field gradient $B_z$ at the magnetic field null point N is large and therefore, the first magnetic sensor 4 strongly receives influence of deviation, etc., due to thermal expansion, etc.

Next, in the case of (B), although the magnetic field gradient $\nabla B_z$ at Z=0 mm is approximately 0 mT/mm, the magnetic field strength at this position is such that $B_z \approx 140$ mT. Therefore, in this case, although the magnetic field gradient in a vicinity of Z=0 mm is small, since this region is not a magnetic field null point, the first magnetic sensor 4 detects a magnetic field generated from the magnet portion 3.

The case of (C) is thus a case where the second correcting portion 12 of flat shape that is short in the front/rear direction and generates a magnetic field of approximately −140 mT is provided in the vicinity of Z=0 in the case of (B). In the case of (C), the magnetic field null point N is positioned at $Z \approx -0.3$ mm and moreover, the magnetic field gradient thereat is such that $\nabla B_z \approx 0$ mT/mm. Therefore, by disposing the first magnetic sensor 4 at this magnetic field null point N, the influence of deviation due to thermal expansion, etc., can be suppressed without detecting the magnetic field generated from the magnet portion 3.

These effects shall be described in terms of principles. First, in the case of (B), the magnet main body portion 5 is separated from the front end portion 3a of the magnet portion 3 by just the front/rear length (approximately 4 mm) of the first correcting portion 11 with respect to the case of (A). Therefore, the magnetic field and the magnetic field gradient that the magnet main body portion 5 generates in the vicinity of Z=0 mm in this case can be regarded as being the same as those at $Z \approx 4$ mm in the case of (A) in the respective graphs of FIG. 7. Also, in FIG. 7Y, the magnetic field gradient at $Z \approx 4$ mm in the case of (A) is $\nabla B_z \approx -20$ mT/mm. From this, it can be said that, in the case of (B), the magnetic field gradient at the front end portion 3A of the magnet portion 3 of the magnet field generated by the magnet main body portion 5 is decreased by the magnet main body portion 5 being separated from the front end portion 3a of the magnet portion 3 by the first correcting portion 11. Yet further, due to the magnetic field generated by the first correcting portion 11, the magnetic field gradient $\nabla B_z$ in the vicinity of Z=0 of the magnetic field generated by the magnet main body portion 5 and the first correcting portion 11 is made substantially 0 T/mm.

Next, the second correcting portion 12 is arranged such that the magnetic field gradient of the magnetic field of the second correcting portion 12 is substantially 0 and such as to cancel out the magnetic field generated by the magnet main body portion 5 and the first correcting portion 11 at the front end portion 3a of the magnet portion 3. If an ideal permanent magnet of circular cylindrical shape is assumed, a magnetic field along its axis is generated in a positive direction toward the front from a front end and toward the rear from a rear end and, on the other hand, toward the rear from the front end and toward the front from the rear end with the magnetic field null point as a boundary, the magnetic field is generated in a negative direction, and this is expressed by a line symmetrical plot where the magnetic field gradient decreases gradually and the change amount becomes substantially zero at a center in the front/rear length of the permanent magnet. This can be confirmed from the plot for the second correcting portion in FIG. 7Y. Therefore, at a position of a center in the front/rear direction of the magnet of circular cylindrical shape, the magnetic field is strongest in the negative direction and the magnetic field gradient is substantially 0. From this, the second correcting portion 12 is made shorter in front/rear length than the magnet main body portion 5 and the first correcting portion 11 and made to fit inside the front end portion 3a of the magnet portion 3. And by designing the magnetic field at the center in the front/rear direction of the second correcting portion 12 such as to cancel out with the magnetic field at the same position of the magnet main body portion 5 and the first correcting portion 11, the magnetic field null point N that is substantially 0 in magnetic field gradient is arranged to be formed at the front end portion 3a of the magnet portion 3. In particular, the inner diameter of the second correcting portion 12 is made shorter than that of the first correcting portion 11 such as to cancel out the magnetic field generated by the magnet main body portion 5 and the first correcting portion 11 at the front end portion 3a of the magnet portion 3.

To simplify the above, with the magnetic field null point N, by matching a front/rear position at which the magnetic field generated by the magnet main body portion 5 reaches a positive peak and a front/rear position at which the magnetic field generated by the second correcting portion 12 reaches a negative peak, the magnetic fields can be canceled out and made substantially 0 and the magnetic field gradient can also be made substantially 0. By setting thus, the magnetic field null point N at which the magnetic field gradient is substantially 0 can be designed in simplified manner. However, it is not necessarily required to match the peaks of the two with each other and the magnetic field null point N may instead be formed in a positional relationship such that a sum of the magnetic field gradients of the two is substantially 0. Also, this can be taken into consideration further when, as in the present embodiment where the first correcting portion 11 is a permanent magnet, the magnet portion 3 has another arrangement that influences the magnetic field. That is, if, by matching the peak of the magnetic field of the second correcting portion 12 and a peak of a magnetic field of the magnet portion 3 besides the second correcting portion 12 (that is, the case of (B) in which the magnet main body portion 5 and the first correcting portion 11 are combined), a sum of the magnetic field strengths of the respective peaks becomes substantially 0, the magnetic field null point N at which the magnetic field gradient is substantially 0 can be formed.

Figure 8A:
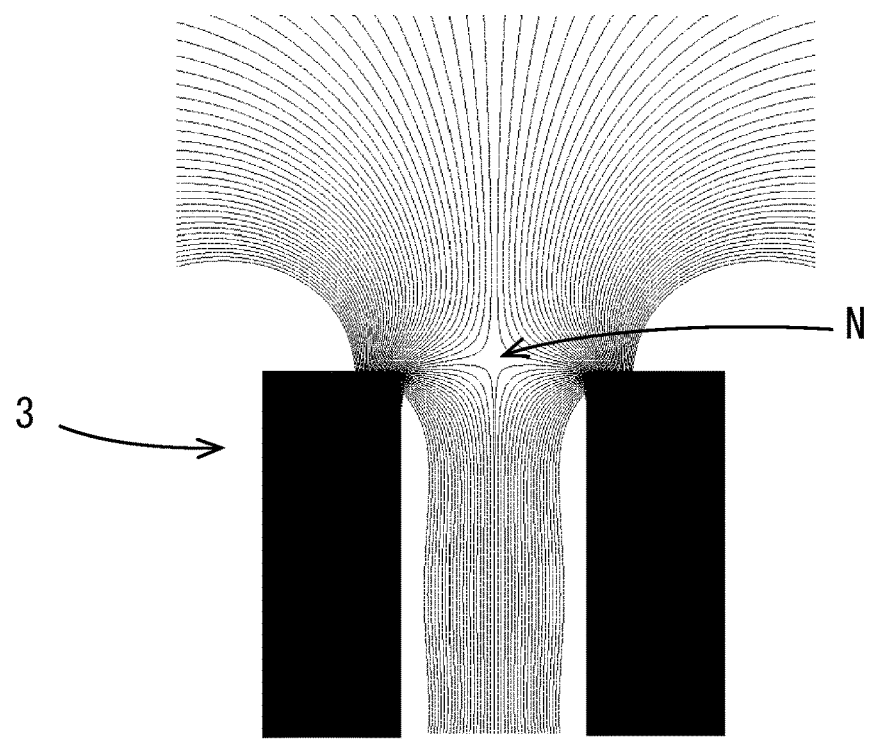
FIG. 8 shows figures of magnetic lines in the magnetic portion (A) in a case where just the magnet main body portion is provided and (C) in a case where the magnet main body portion and a correcting portion are provided.
Figure 8C:
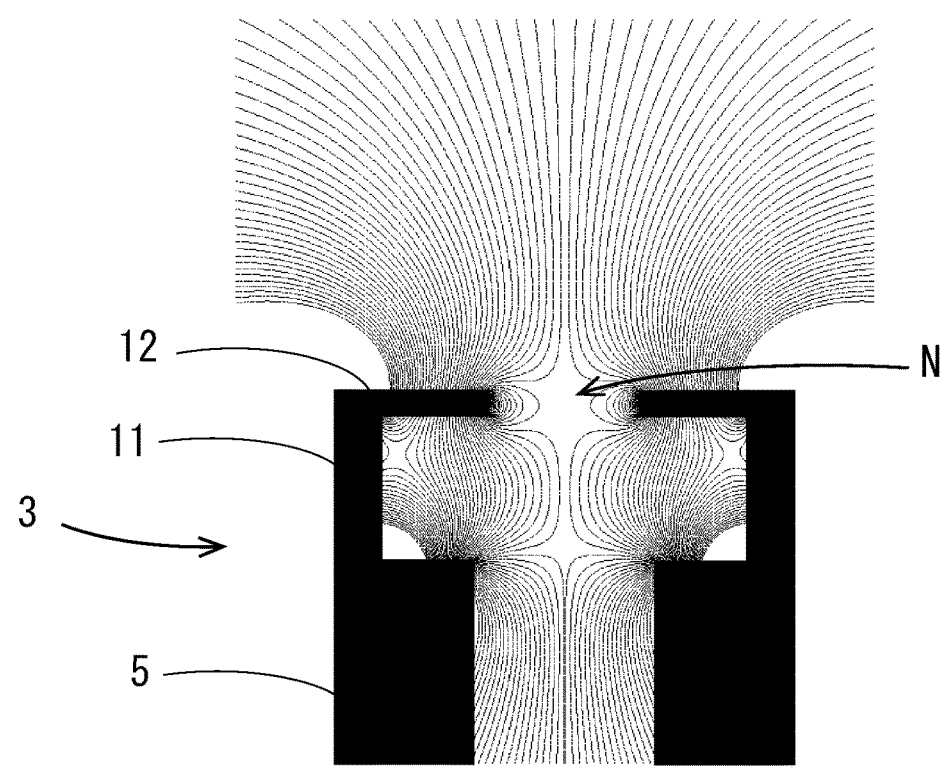
Figure 9:
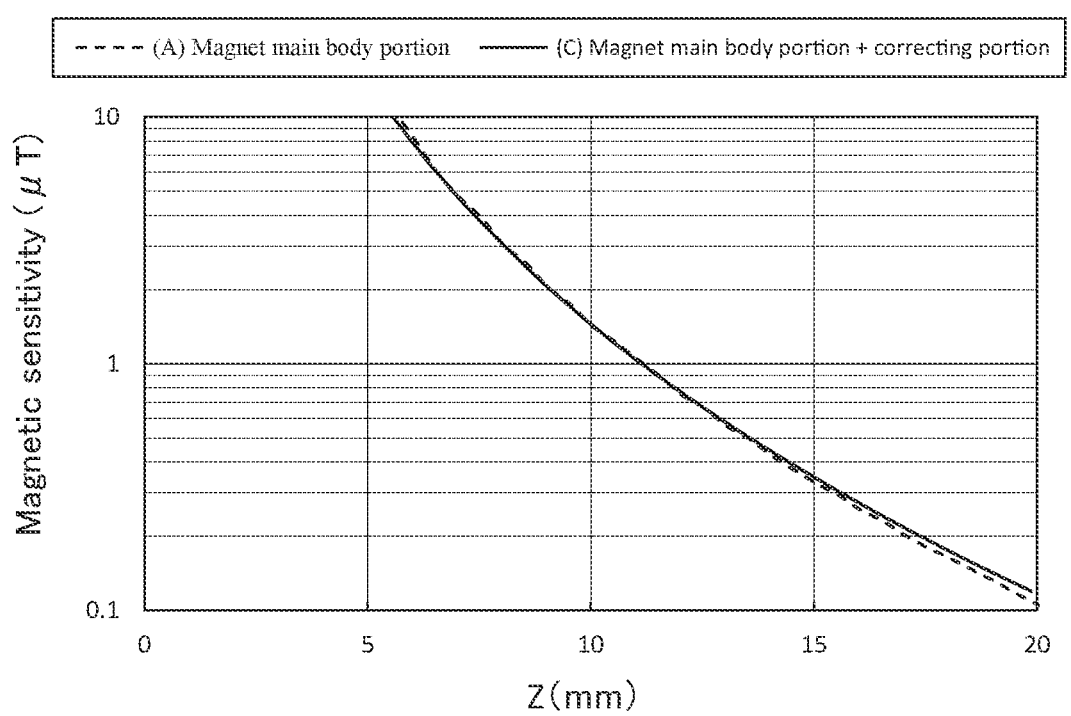
FIG. 9 is a graph showing magnetic sensitivities in front of the magnetic portion for the respective magnetic portions.
Figure 10A:
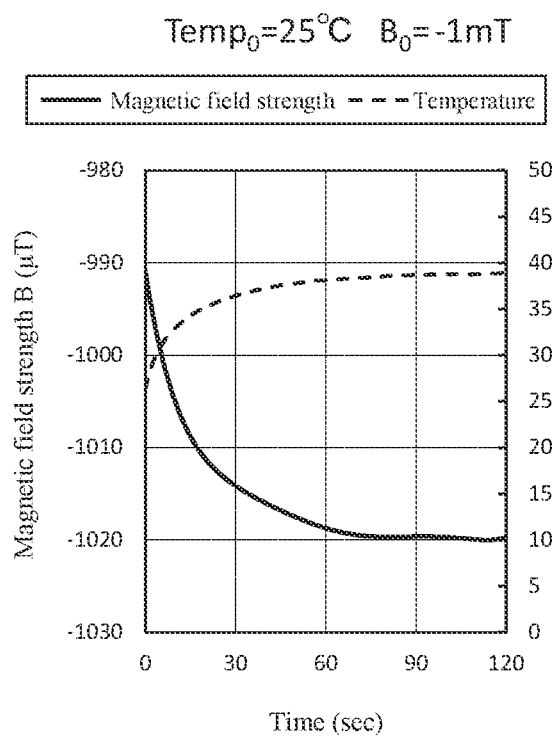
FIG. 10 shows graphs showing changes in a detection value of a magnetic sensor when an initial temperature is set to 25° C. for cases where an applied magnetic field strength is (A) −1 mT, (B) 0 mT, (C) 1 mT, and (D) 2 mT.
Figure 10B:
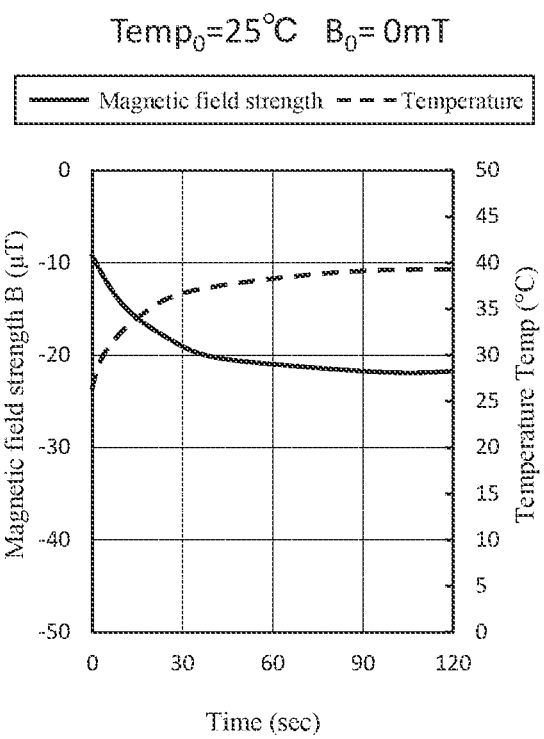
Figure 10C:
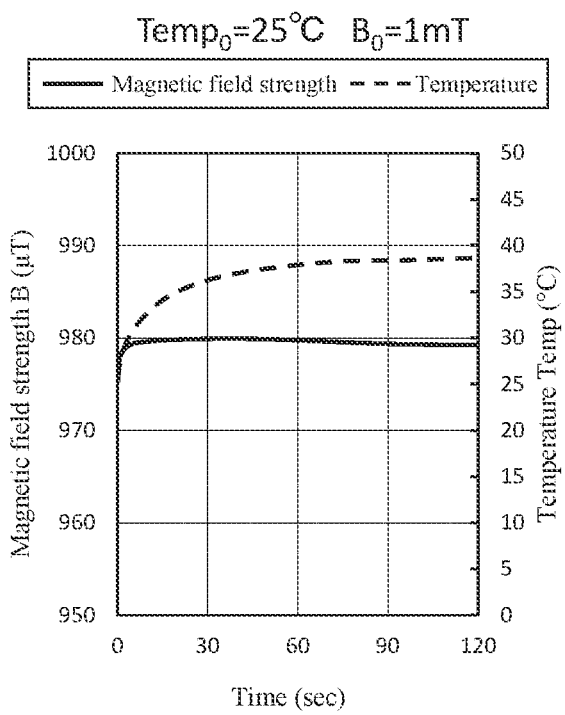
Figure 10D:
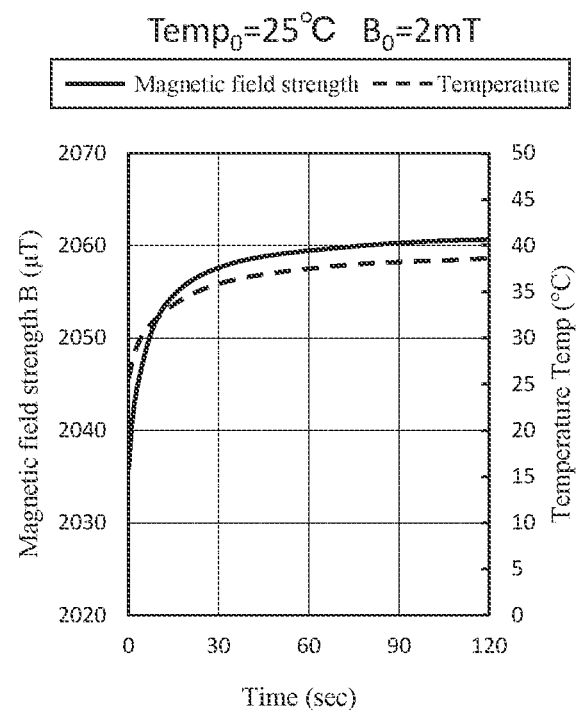
Figure 11A:
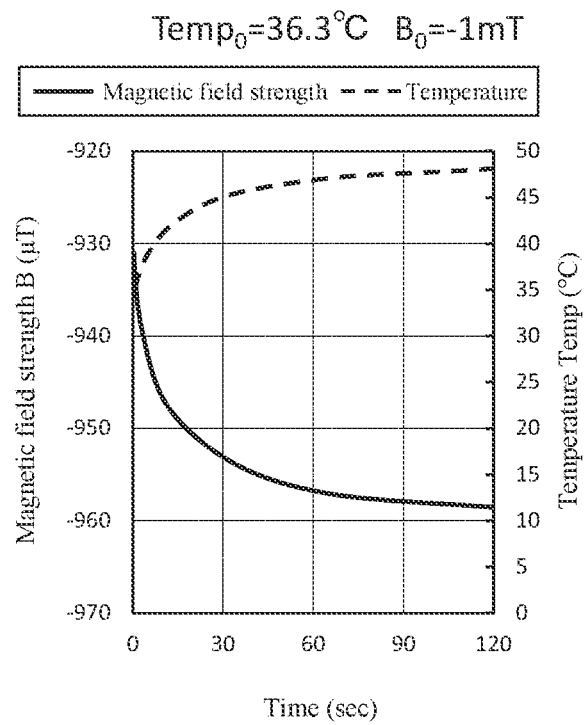
FIG. 11 shows graphs showing changes in the detection value of the magnetic sensor when the initial temperature is set to 36.3° C. for cases where the applied magnetic field strength is (A) −1 mT, (B) 0 mT, (C) 1 mT, and (D) 2 mT.
Figure 11B:
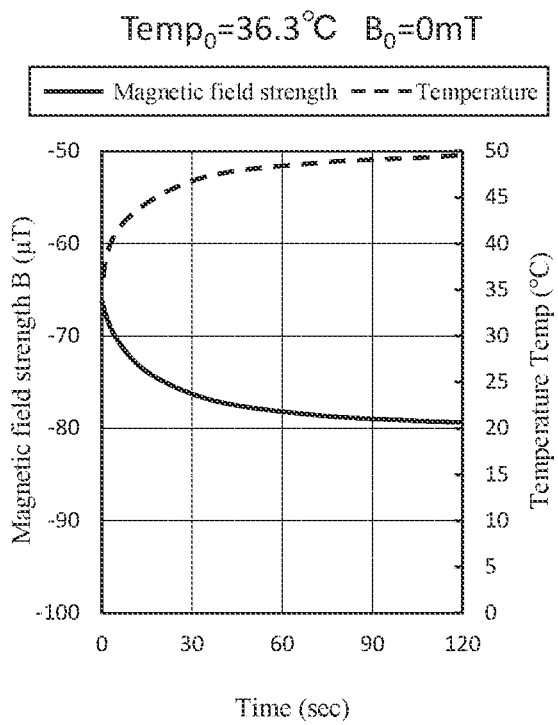
Figure 11C:
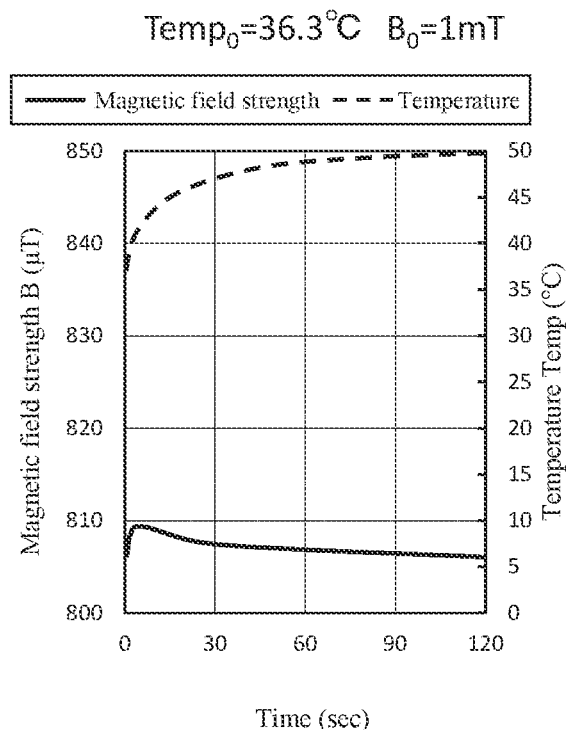
Figure 11D:
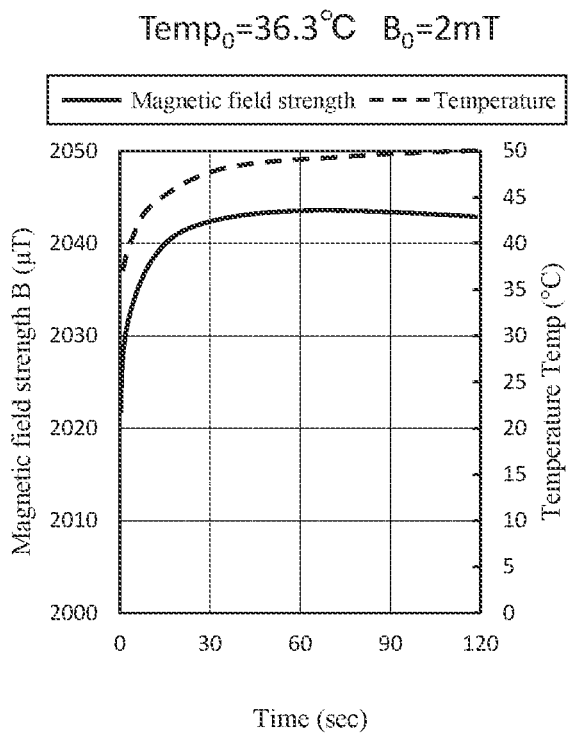

FIG. 8 shows magnetic lines in the above-described case of (A) and case of (C), respectively. From a comparison, it can be understood that with respect to the case of (A), there are less magnetic lines in a vicinity of the front end of the magnet portion 3. Further, since the magnetic lines in front of the respective magnet portions 3 are of approximately the same density, it can be understood that the magnetic field strengths are equivalent. In regard to this point, FIG. 9 shows changes in magnetic sensitivity in accordance with distance (Z) from the front end portion for each of the magnet portions 3. As is clear from this figure, the magnetic sensitivities of the two are substantially equal in the vicinity of Z=10 mm. From the above, it can be said that in the case of (C), a magnetic sensitivity equivalent to that of an ordinary circular columnar magnet as in the case of (A) is provided even with the magnetic field gradient in the vicinity of the magnetic field null point N being reduced. To secure a magnetic sensitivity that is approximately equal, whereas the front/rear length of the magnetic portion 3 in the case of (A) is approximately 12 mm, the magnetic portion 3 in the case of (C) is made elongate and approximately 38 mm in front/rear length, as described above. In addition, signal strength can also be secured by making the diameter of the magnet portion 3 large, adopting a magnet of stronger magnetic force, etc. Therefore, with the magnet portion 3 according to the present embodiment, detection of high sensitivity is enabled by the first magnetic sensor 4 because the magnetic field gradient at the magnetic field null point N is reduced while maintaining the signal strength. This also means that since noise (N) generated due to positional change can be reduced while maintaining the signal strength (S), an SN ratio can be increased. Since influence of noise is thus decreased in detection by the first magnetic sensor 4, detection with high sensitivity can be performed over a greater distance.

Furthermore, the front/rear length of the magnet main body portion 5 is changed in each of the cases of (A) to (C) as described above, and this is done to compensate for decrease in the magnetic field in front that accompanies the separation of the magnet main body portion 5 rearward with respect to the front end portion 3a of the magnet portion 3. That is, even when the magnet main body portion 5 is disposed rearward, it is necessary to design such that the magnet portion 3 as a whole is capable of appropriately magnetizing the magnetic body in front. A standard for this can be set as appropriate in accordance with the detection subject and, for example, by setting the front/rear length of the magnet main body portion 5 (or the front/rear length of the magnet portion 3) such that a magnet field at Z=10 mm satisfies B>50 mT, it is made possible to magnetize the magnetic body in front appropriately.

Also, from a standpoint of reducing the influence due to deviation of the first magnetic sensor 4, it is not necessarily required to make the magnetic field gradient at the magnetic field null point N substantially 0. That is, the magnetic field gradient at the magnetic field null point N can be reduced and the influence due to deviation can be reduced by decreasing the magnetic field gradient of the magnetic field generated by the magnet main body portion 5 at the front end portion 3a of the magnet portion 3 by separating the magnet main body portion 5 from the front end portion 3a of the magnet portion 3 by the first correcting portion 11. However, in doing so, the magnetic field gradient of the magnetic field generated by the correcting portion 6 itself must also be considered. In other words, by separating the magnet main body portion 5 rearward from the front end portion 3a of the magnet portion 3, especially in accordance with the magnetic field gradient of the magnetic field generated by the second correcting portion 12, the first correcting portion 11 can adjust the magnetic field gradient, at the magnetic field null point N, of the magnetic field generated by an entirety of the magnet portion 3 and reduce the magnetic field gradient at the magnetic field null point N. Even from this point, the present invention is not restricted to the specific numerical values, shape, etc., described above.

Further, although the magnet main body portion 5 and the second correcting portion 12 are required to be permanent magnets, the first correcting portion 11 is not required to be a permanent magnet. That is, the first correcting portion 11 is a component that separates the magnet main body portion rearward from the front end portion 3a of the magnet portion 3 to adjust the magnetic field gradient, at the magnetic field null point N, of the magnetic field generated by the magnet main body portion 5 and is thus not required to be a permanent magnet itself and may also be a nonmagnetic body. Or, if the magnet main body portion 5 and the second correcting portion 12 that are disposed in an appropriate positional relationship are fixed by the cover body 2a and the shaft 9, the first correcting portion 11 does not necessarily have to be provided.

The first magnetic sensor 4 is disposed at the magnetic field null point N described above and detects the magnetic field of the magnetic body in front. With magnetic poles of the first magnetic sensor 4, as with the magnetic poles of the magnet portion 3, a front side is the S pole. Since the magnetic field gradient $B_z$ is also substantially 0 at the magnetic field null point N, a sensor of high sensitivity such as an MI element, a GMR sensor, a GSR sensor, or a diamond sensor can be adopted besides a Hall element as the first magnetic sensor 4. Also, the first magnetic sensor 4 is not restricted to one and a plurality of first magnetic sensors 4 can also be provided. Especially in the present embodiment, the magnetic field gradient at the magnetic field null point is low and therefore, even when a plurality of magnetic sensors are provided, an installation space can be secured easily. A signal due to the first magnetic sensor 4 is transmitted through the wiring code 10 to the controller inside the case portion 8. Furthermore, if the front/rear length of the second correcting portion 12 is made short, the magnetic field null point N is formed further in front and the first magnetic sensor 4 can be disposed further in front correspondingly and therefore a detection range can be widened.

The magnetic body detecting device 1 is preferably arranged to include a second magnetic sensor 13 as shown in FIG. 1. The second magnetic sensor 13 is a magnetic sensor for detecting geomagnetism and that which is the same as the first magnetic sensor 4 is adopted. The second magnetic sensor 13 is disposed at a position further rearward than a rear end of the magnet portion 3 inside the shaft 9 and in the same direction as the first magnetic sensor 4. By being separated from the magnet portion 3, the second magnetic sensor 13 can detect geomagnetism in a state where influence of the magnet portion 3 is suppressed. And by performing correction by subtracting a detection value of the second magnetic sensor 13 from a detection value of the first magnetic sensor 4, a detection value that is eliminated of influence of geomagnetism can be acquired.

Or, the second magnetic sensor 13 may be disposed adjacent to the first magnetic sensor 4 and in opposite direction to the first magnetic sensor 4. By arranging thus, a mutual difference between the detection values can be detected as geomagnetism and a detection value that is eliminated of influence of geomagnetism can thus be acquired likewise. In this case, the first magnetic sensor 4 and the second magnetic sensor 13 are preferably disposed symmetrically.

Also, the position at which the first magnetic sensor 4 is disposed is not necessarily restricted to the magnetic field null point N and disposition at a position of a desired magnetic field strength is possible. The magnetic field gradient should then be adjusted and reduced at the position of the desired magnetic field strength. That is, although in the embodiment described above, the magnetic field strength is made substantially 0 by combining the positive peak of the combined magnetic field strength of the magnet main body portion 5 and the first correcting portion 11 and the negative peak of the magnetic field strength of the second correcting portion 12, the magnetic field strength at the position where the magnetic field gradient is substantially 0 can be adjusted, for example, by changing the magnetic field strength of the negative peak of the second correcting portion 12.

For example, a case such as the following can be assumed for disposing the first magnetic sensor 4 at a specific position of desired magnetic field strength that is not the magnetic field null point N. Among magnetic sensors, there are those that change in detection value in accompaniment with temperature change. Also, there are cases where a magnetic sensor rises in temperature in accompaniment with its own heat generation or approaching of a living body, etc., during use and in this case, it is desired to correct the detection value in accordance with the temperature of the magnetic sensor. Here, depending on the magnetic sensor, there is a case where a temperature change of the magnetic sensor changes in accordance with a magnetic field strength applied to the magnetic sensor. In such a case, it is preferable at times, in performing a desired correction, to apply a magnetic field of predetermined strength to the magnetic sensor in advance, that is, to dispose the magnetic sensor not at the magnetic field null point but at a position of desired magnetic field strength.

This point shall be described by illustrating a specific example based on FIGS. 10 to 12. FIG. 10 shows graphs showing changes in a temperature Temp and a detection value B (µT) of a magnetic sensor (a Hall IC), with a magnetic field of predetermined magnetic field strength $B_{bias}$ (mT) applied thereto at an initial temperature $Temp_0=25°$ C., when it is supplied with electricity. The temperature change is that caused by heat generation in accompaniment with the supplying of electricity to the magnetic sensor. FIGS. 10A to 10D are graphs for cases where $B_{bias}=-1$ mT, 0 mT, 1 mT, and 2 mT, respectively. FIG. 11 shows graphs showing the changes when the same trials were carried out in a case where the initial temperature $Temp_0=36.3°$ C. From these results, it can be understood that, with this magnetic sensor, even with the same change amount of temperature, the change amount of the detection value B differs according to the applied magnetic field strength $B_{bias}$. More specifically, there is a tendency that the greater the $B_{bias}$, the greater the change amount of the detection value with respect to the change amount of temperature as well.

Figure 12A:
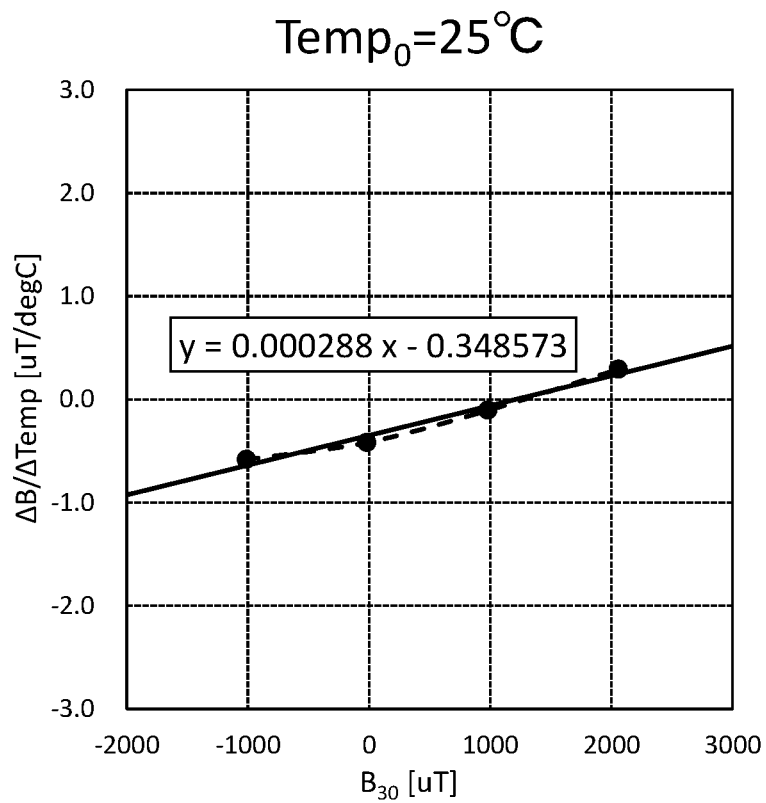
FIG. 12 shows graphs showing relationships of the magnetic field strength applied to the magnetic sensor and a ratio of change amount of temperature with respect to change amount of detection value with (A) being that in the case of FIG. 10 and (B) being that in the case of FIG. 11.
Figure 12B:
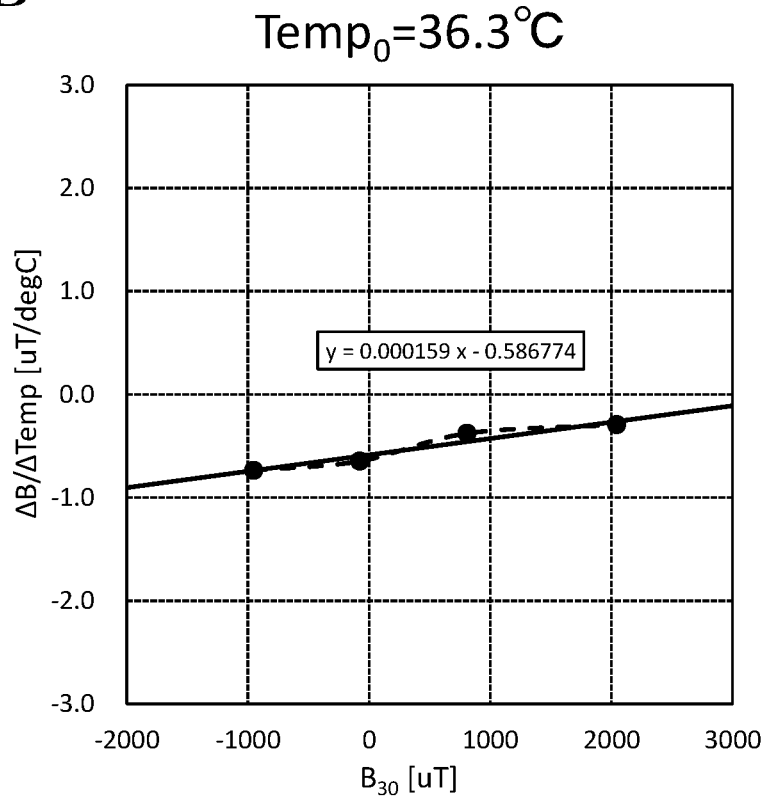

FIG. 12A is a graph in which, based on FIGS. 10A to 10D, a detection value $B_{30}$ 30 seconds after the supplying of electricity is plotted on the abscissa axis and a ratio of the change amount $\Delta B$ of the detection value B and the change amount $\Delta Temp$ of the temperature Temp from 30 seconds to 120 seconds after the supplying of electricity is plotted on the ordinate axis for the case where the initial temperature $Temp_0=25°$ C. Approximation of the four points by a linear function results in $\Delta B/\Delta Temp=0.000288B_{30}-0.348573$. Here, the $B_{30}$ for which $\Delta B/\Delta Temp=0$ is approximately 1210 µT. Based on this value of $B_{30}$ and, for example, deeming this value to be the applied magnetic field strength $B_{bias}$, it can be assumed that by setting $B_{bias}=1.210$ mT, the detection value becomes substantially fixed and stable detection is thus enabled from after elapse of 30 seconds after the supplying of electricity even if a temperature change occurs in the magnetic sensor. Similarly, FIG. 12B is a graph in which, based on FIGS. 11A to 11D, the ratio of $\Delta B$ and $\Delta Temp$ is plotted for the case where the initial temperature $Temp_0=36.3°$ C. In this case, $\Delta B/\Delta Temp=0.000159B_{30}-0.586774$, the $B_{30}$ for which $\Delta Temp=0$ is approximately 3690 µT, and it is assumed that setting $B_{bias}=3.690$ mT is preferable.

Since influence on the detection value due to temperature change thus occurs depending on the magnetic sensor, it is desired to reduce this influence. In this case, the influence of temperature change can be reduced at times by applying a magnetic field of a predetermined magnetic strength $B_{bias}$ on the magnetic sensor in advance. In this case, it is preferable, for example, when the initial temperature $Temp_0=25°$ C., to dispose the magnetic sensor not at the magnetic field null point but at a specific position where $B=1.210$ mT as the desired magnetic field strength. Then, based on the arrangement described above, the magnet portion 3 should be arranged such that the magnetic field gradient is substantially zero at the specific position being of the desired magnetic field strength.

Figure 13A:
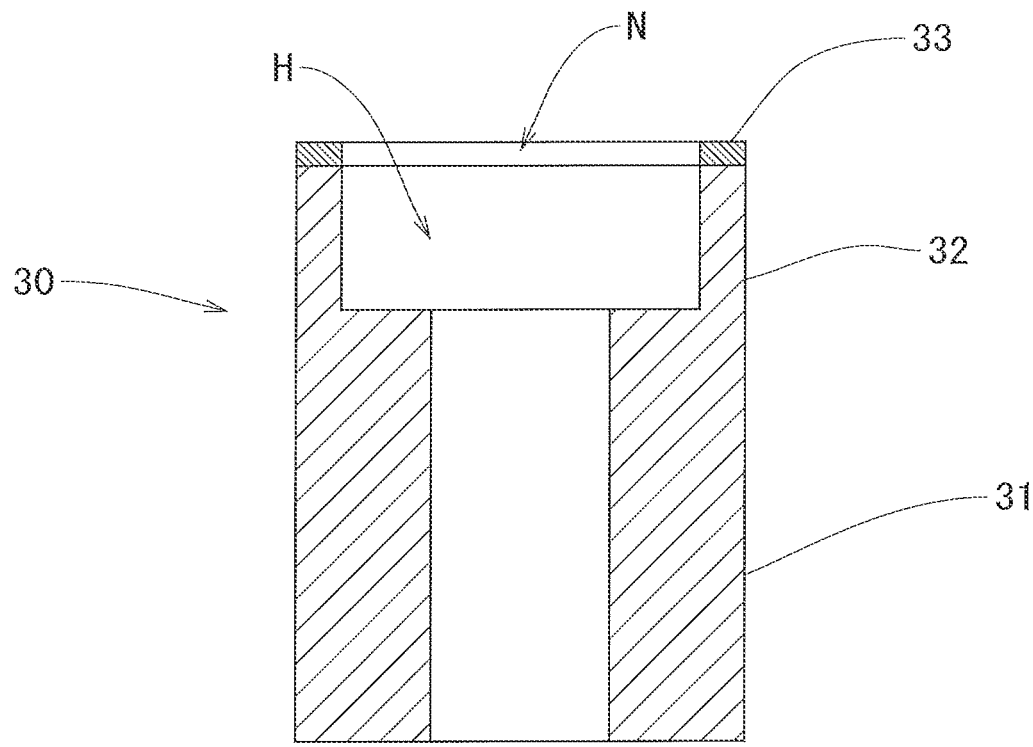
FIG. 13A and FIG. 13B are both front sectional views of modifications of the magnet portion.

Next, modifications of the magnet portion 3 shall be described. In the embodiment describe above, the magnet portion 3 is arranged as that where the magnet main body portion 5 and the correcting portion 6 are provided by changes in internal shape of a single magnet material. However, the magnet portion 3 may instead be arranged using respectively different magnets as the magnet main body portion 5 and the first and second correcting portions 11 and 12. For example, as shown in FIG. 13A, a magnet portion 30 can be arranged with a magnet main body portion 31 and a first correcting portion 32 being a single magnet and a second correcting portion 33 being another magnet. In this case, by arranging the magnet main body portion 31 and the first correcting portion 31 to be of the same shapes as in the embodiment described above and meanwhile adopting an appropriate magnet that is greater in residual magnetic flux density than the magnet of the magnet main body portion 31 and the first correcting portion 32 as the second correcting portion 33, an inner diameter thereof can be made equal to an inner diameter of the magnet main body portion 31. The front end portion of the shaft 9 is thus not required to be changed in shape along the inner diameter of the second correcting portion 33 and adjustment of disposition of the first magnetic sensor 4 is facilitated. Furthermore, the hollow portion H in this case is a space of simple circular cylindrical shape that is wider in inner diameter than the magnet main body portion 31.

Figure 13B:
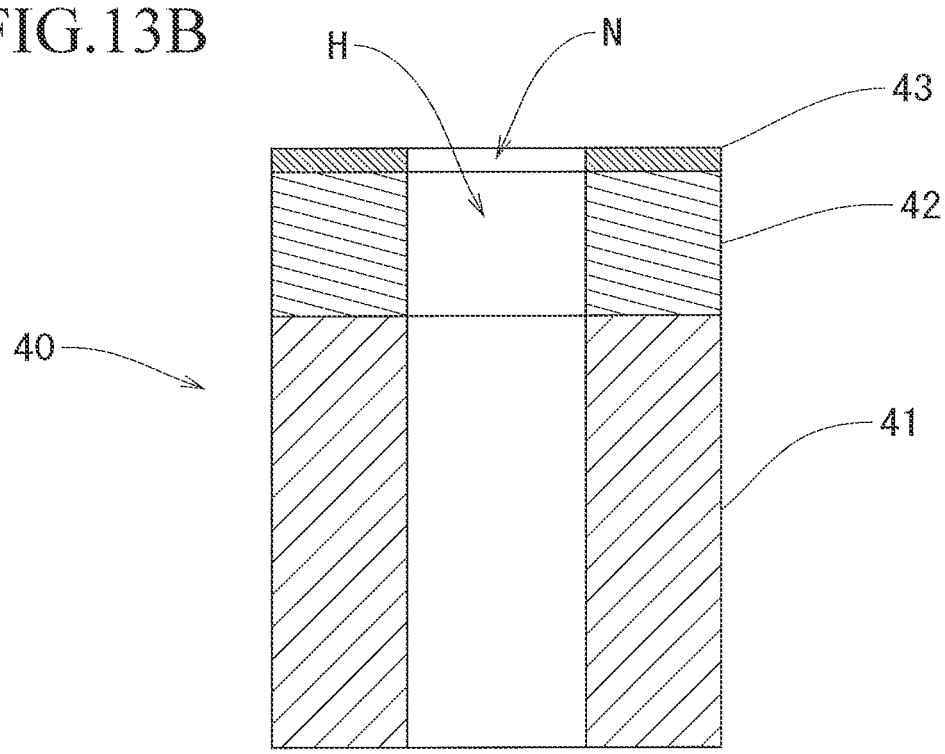

Also, as shown in FIG. 13B, a permanent magnet 40 can be arranged with a magnet main body portion 41, a first correcting portion 42, and a second correcting portion 43 respectively being different magnets. In this case, the first correcting portion 42 is made a magnet of smaller residual magnetic flux density than the magnet main body portion 41 and the second correcting portion 43 is made a magnet of greater residual magnetic flux density than the first correcting portion 42. By adjusting these magnets, inner diameters of the first correcting portion 42 and the second correcting portion 43 can be made equal to an inner diameter of the magnet main body portion 41. Furthermore, the hollow portion H in this case is a space of simple circular columnar shape that is equal in inner diameter to the magnet main body portion 41.

As illustrated by these embodiments, in the magnet portion in the present invention, magnitude relationships of the respective inner diameters of the magnet main body portion, the first correcting portion, and the second correcting portion are not such that are defined univocally. Various design modifications are possible in accordance with the strength of the magnet and the front/rear length of each portion. Also, the outer diameters of the respective portions can also be made to differ respectively.

Further, although with the embodiment (and modifications) described above, the magnet main body portion 5, the first correcting portion 11, and the second correcting portion 12 that are the respective constituents of the magnet portion 3 are all of circular cylindrical shape, the shape is not restricted thereto. For example, although the magnet main body portion 5 is of circular cylindrical shape in order to insert the shaft 9 through, if this is not required, it can be of a circular cylindrical shape that is solid. Further, the magnet main body portion 5 also does not have to be a single permanent magnet and may instead be arranged as a combination of a plurality of permanent magnets, etc. In this case, the plurality of permanent magnets constituting the magnet main body portion 5 may be joined to or separated from each other. Also, the respective constituents of the magnet portion 3 are not required to be of circular shape in cross-sectional shape in a plane horizontal to the Z axis and may be of any of various shapes such as, for example, a polygonal shape, a star shape, an elliptical shape, etc. Although it is preferable in terms of design for this cross-sectional shape to be one having symmetry with respect to the Z axis, there is no restriction thereto. The shapes of the respective constituents of the magnet portion 3 thus make up one factor in adjusting the magnetic field gradient at the magnetic field null point N by correcting the magnetic field in front of the magnet main body portion 5 by the correcting portion 6 and can also be designed appropriately in accordance with adjustment of the strength of the magnet, etc., and are therefore not restricted to the specific shapes described above.

In the first embodiment arranged as described above, the magnetic body detecting device 1 includes the magnet portion 3 constituted of the magnet main body portion 5 that is a permanent magnet and the correcting portion 6 disposed in front of the magnet main body portion 5 and correcting the magnetic field generated from the magnet main body portion 5. Also, the correcting portion 6 cancels out the magnet field generated at the front end portion 3a of the magnet portion 3 by the magnet main body portion 5 to form the magnetic field null point N of substantially 0 magnetic field strength as the as the specific position being of the desired magnetic field strength. Especially in this case, the magnetic field null point is formed by the second correcting portion 12, constituted of the permanent magnet disposed in front of the first correcting portion 11, canceling out the magnet field at the front end portion 3a of the magnet portion 3 generated by the entirety of the magnet portion 3 excluding the second correcting portion 12. The correcting portion 6 further separates the magnet main body portion 5 from the front end portion 3a of the magnet portion 3 by the first correcting portion 11 to adjust and reduce the magnetic field gradient at the front end portion 3a of the magnet portion 3 of the magnetic field generated by the magnet main body portion 5. In this process, by separating the magnet main body portion 5 from the front end portion 3a of the magnet portion 3 in accordance with the magnetic field gradient of the magnet field generated by the correcting portion 6 to adjust the magnetic field gradient generated by the entirety of the magnet portion 3 at the magnetic field null point N, it is made possible to reduce the magnetic field gradient at the magnetic field null point N. The magnetic field gradient at the magnetic field null point N is adjusted such as to be reduced especially in comparison to the magnetic field null point N in a case where the magnet portion 3 is constituted of just the magnet main body portion 5 (such as in the case of FIG. 6A). By then disposing the first magnetic sensor 4 at the magnetic field null point N, influence of deviation of the first magnetic sensor 4 or the magnet portion 3 due to thermal expansion, etc., due to temperature change accompanying approaching of the subject, etc., can be reduced.

Also, the magnetic field null point N that is the specific position is formed by matching the respective front/rear positions of the positive peak of the magnetic field generated by the magnet portion 3 excluding the second correcting portion 12 (that is, the magnet main body portion 5 and the first correcting portion 11) and the negative peak of the magnetic field generated by the second correcting portion 12. By thus matching different peaks with each other, it is made possible to easily design the specific position at which the magnetic field gradient is made substantially 0 and moreover, by matching the positive and negative portions thereof, the magnetic field null point N can be designed easily.

Also, by making the front/rear length of the second correcting portion 12 shorter than the front/rear length of the first correcting portion 11, the magnetic field null point N can be disposed as much in front as possible. Further, the hollow portion H is formed in the interior of the correcting portion 6 by the first correcting portion 11 having the circular cylindrical shape of larger inner diameter than the inner diameter of the magnet main body portion 5 and the second correcting portion 12 having the circular cylindrical shape of smaller inner diameter than the inner diameter of the first correcting portion 11. By arranging such shapes, it is made possible to reduce the magnetic field gradient at the magnetic field null point by processing of a single magnet.

Figure 14:
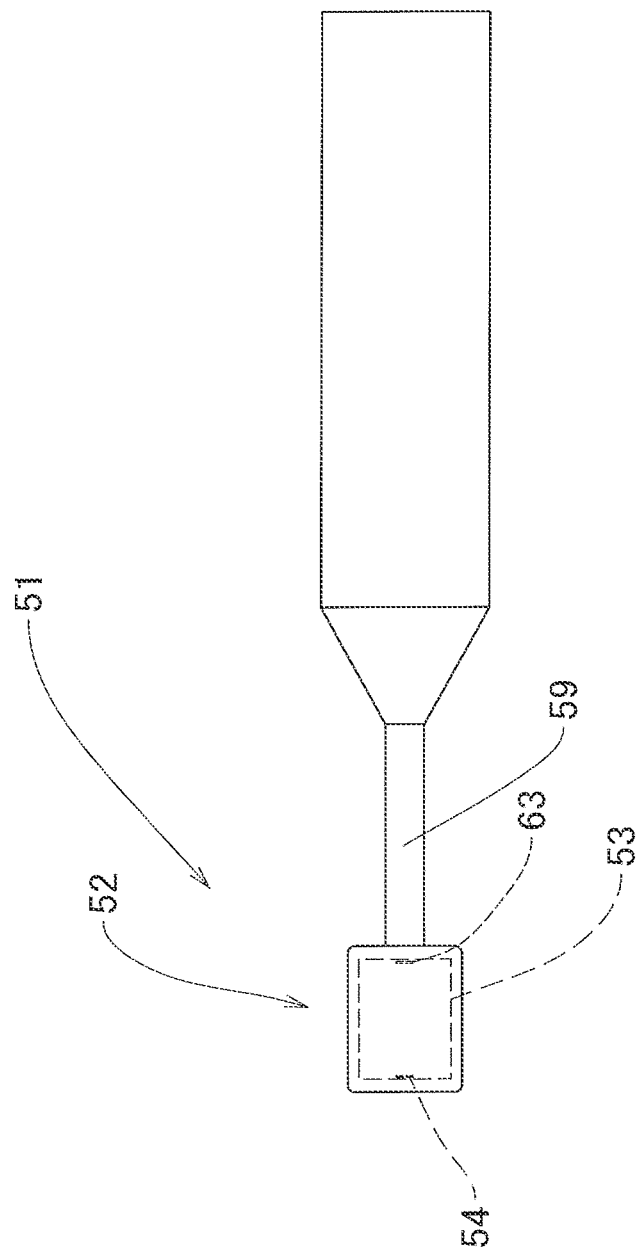
FIG. 14 is an overall view of a magnetic body detecting device according to a second embodiment.
Figure 15:
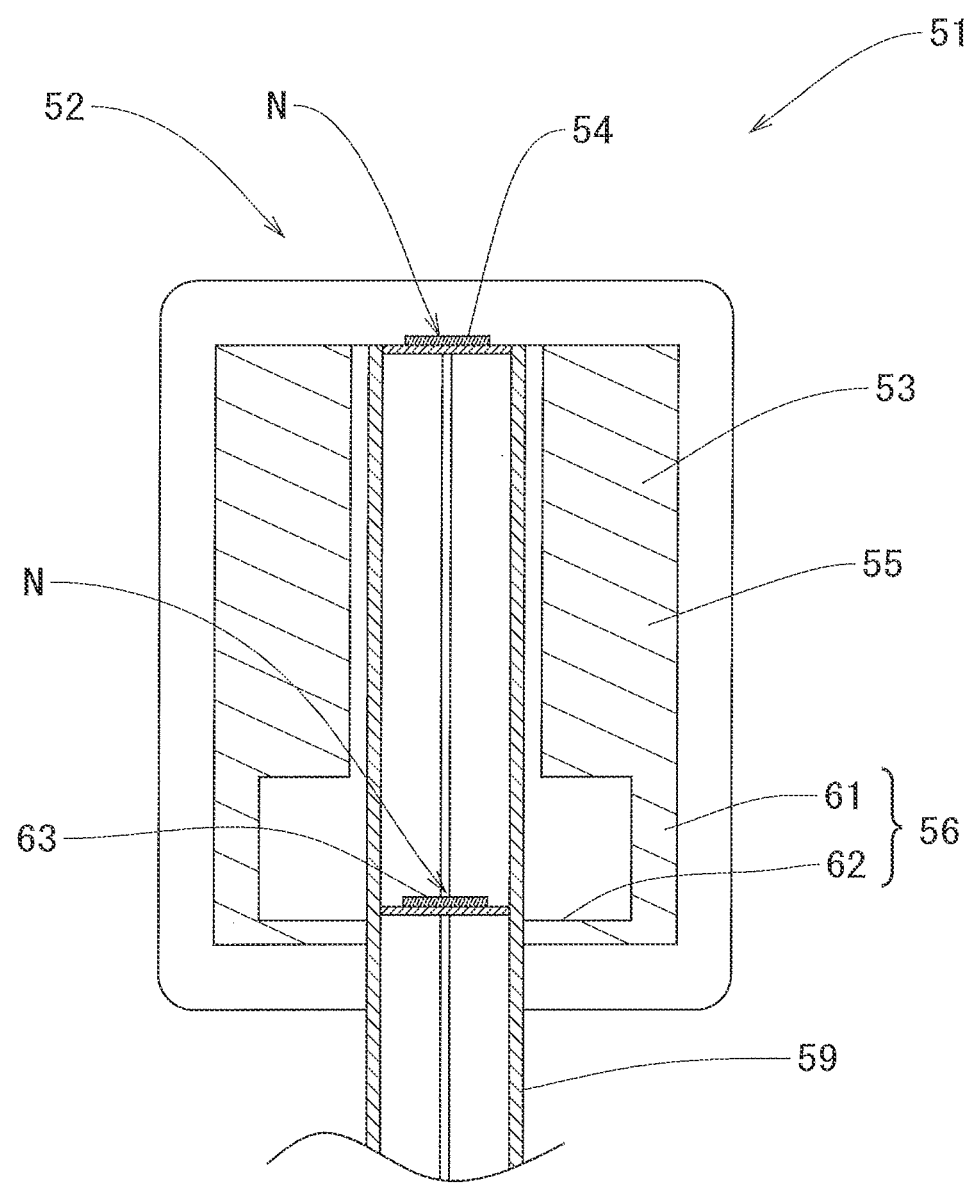
FIG. 15 is a sectional view of a detecting portion of the magnetic body detecting device according to the second embodiment.

Next, a second embodiment of a magnetic body detecting device according to the present invention shall be described based on FIGS. 14 and 15. The magnetic body detecting device 51 according to the second embodiment differs from the magnetic body detecting device 1 according to the first embodiment in the structure of the magnet portion and the disposition of the magnetic sensor but has the same arrangements in regard to the other points. Therefore, the arrangements that differ shall mainly be described and description of the arrangements that are same shall be omitted as appropriate.

With the magnetic body detecting device 51 according to the second embodiment, a detecting portion 52 includes, as a magnet portion 53, that with which the front and rear of the magnet portion 3 according to the first embodiment are reversed. That is, a correcting portion 56 is provided at a rear end portion of a magnet main body portion 55 with there being disposed a second correcting portion 62 at a rear end of the magnet portion 53 and a first correcting portion 61 between the magnet main body portion 55 and the second correcting portion 62.

Also, the magnetic body detecting device 51 includes, as magnetic sensors, a first magnetic sensor 54 disposed at a front end portion and a second magnetic sensor 63 disposed at a rear end portion of the magnet portion 53. The first magnetic sensor 54 is used for detecting a magnetic field of a magnetic body of a detection subject. On the other hand, the second magnetic sensor is used to detect geomagnetism in a state of eliminating influence of the magnet portion 53. Also, the first magnetic sensor 54 and the second magnetic sensor 63 are both arranged to be disposed at magnetic field null points N of substantially the same magnetic field strength.

When the second magnetic sensor 63 that is a geomagnetism sensor is thus disposed at a specific position of a desired magnetic strength such as the magnetic field null point N that is reduced in magnetic field gradient, geomagnetism can be detected inside the magnet portion 53 without being influenced thereby and can thus be constituted of a sensor of high sensitivity. Moreover, since there is no need to dispose the geomagnetic sensor at the rear of the magnet portion 53, a front/rear length of a shaft 59 can be shortened and the device can also be made compact.

Furthermore, as in the first embodiment, the inner diameter of the first correcting portion 11 is smaller than the inner diameter of the magnet main body portion 55 and therefore the shaft 9 is made to have the inner diameter of the first correcting portion 62 at least at portion that is inserted through the magnet portion 53. When arranged thus, an inner periphery of the magnet main body portion 55 and the shaft 59 are separated and therefore, a gap agent that fills the gap can be fitted in from a tip side, etc. Or, the shaft 59 can be constituted of a plurality of members and arranged to sandwich inner peripheral end portions of the second correcting portion 62 from the front and rear.

Figure 16:
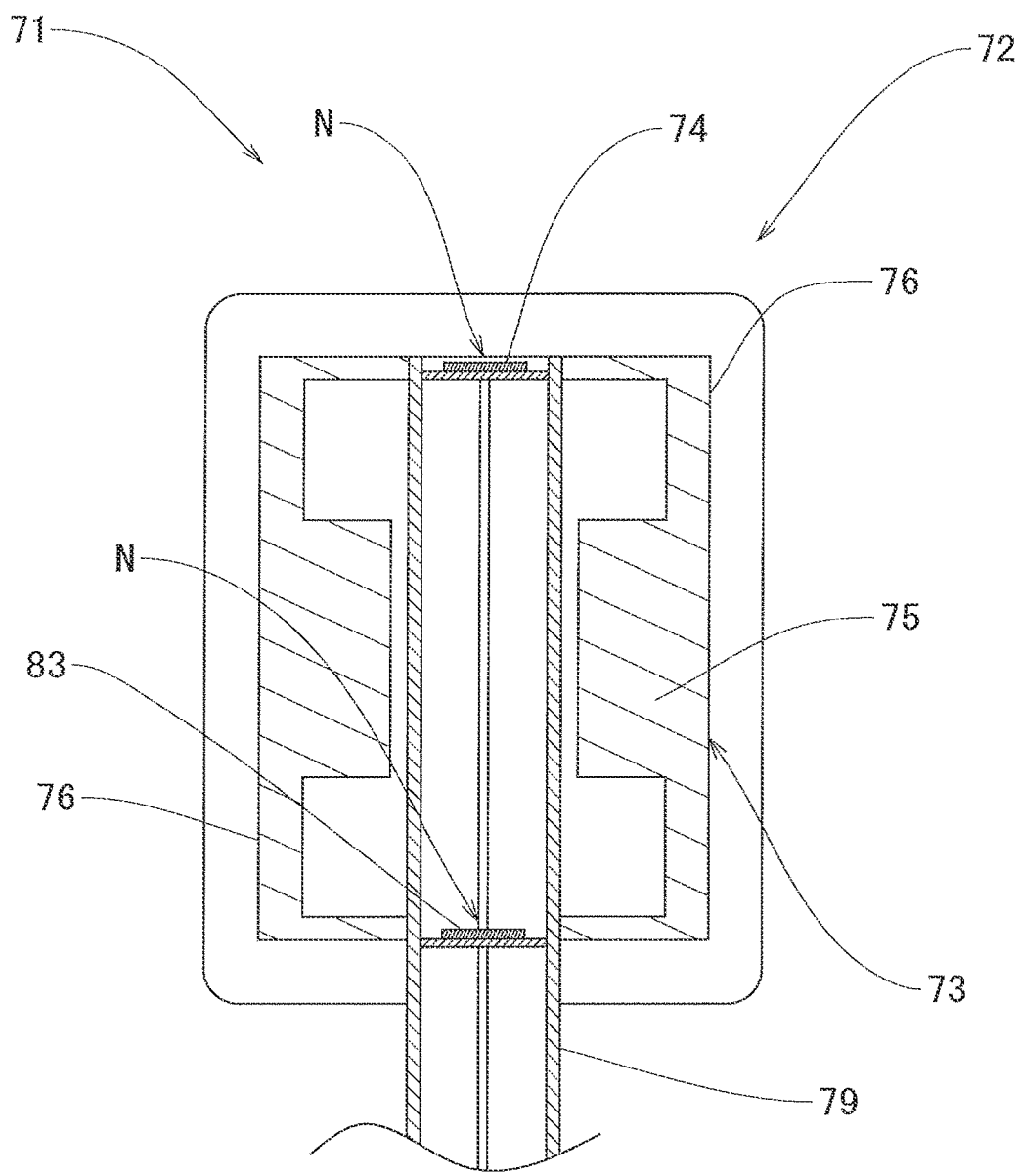
FIG. 16 is a sectional view of a detecting portion of a magnetic body detecting device according to a third embodiment.

Next, a third embodiment of a magnetic body detecting device according to the present invention shall be described based on FIG. 16. The magnetic body detecting device 71 according to the third embodiment includes a first magnetic sensor 74 disposed at a front end portion and a second magnetic sensor 83 disposed at a rear end portion of a detecting portion 72. Further, correcting portions 76 are disposed at both front and rear end portions of a magnet portion 73 and an elongate magnet main body portion 75 is disposed therebetween. The first magnetic sensor 74 and the second magnetic sensor 83 are respectively disposed at magnetic field null points N that are specific positions at which the magnetic field strength, as the desired magnetic field strength, is 0.

The first magnetic sensor 74 and the second magnetic sensor 83 are thus both disposed at the magnetic field null points N at which the magnetic field gradients are reduced by the correcting portions 76 and therefore both magnetic sensors can be reduced in influence due to noise such as to be capable of detection of high sensitivity and also enable making of the device compact through shortening of a front/rear length of a shaft 79.

Furthermore, obviously, even in the second embodiment and the third embodiment, the magnet main body portion and the respective correcting portions can be arranged as different magnets that constitute a permanent magnet as in the modifications of the first embodiment shown in FIGS. 13A and 13B. In the third embodiment, just the correcting portion either at the front or rear can be arranged as a different magnet from the magnet main body portion and both of those at the front and rear can be arranged as different magnets.

Besides the above, the present invention is not restricted to just the embodiments and modifications described above and is also not restricted to the specific forms and numerical values. Also, although the present invention can mainly be used in sentinel lymph node biopsy of breast cancer, application thereof is not restricted thereto and it can be used for detection of a magnetic body in various parts inside a living body and can also be used on a subject other than a living body.

INDUSTRIAL APPLICABILITY

The present invention can be utilized in a technical field of a magnetic body detecting device used in sentinel lymph node biopsy, etc.

REFERENCE SIGNS LIST

1 Magnetic body detecting device
2 Detecting portion
3 Magnet portion
3a Front end portion
4 First magnetic sensor
5 Magnet main body portion
6 Correcting portion
11 First correcting portion
12 Second correcting portion
13 Second magnetic sensor
H Hollow portion
N Magnetic field null point (specific position)

The invention claimed is:
1. A magnetic body detecting device comprising:
a detecting portion at a front end that, in a state of being in contact with or proximity to a subject, detects a magnetic body; and
wherein the detecting portion includes
a magnet portion for magnetizing the magnetic body and
a magnetic sensor for detecting magnetism,
the magnet portion includes
a magnet main body portion that is a permanent magnet and
a correcting portion disposed at least at one of either a front or a rear of the magnet main body portion and correcting a magnetic field generated from the magnet main body portion and
forms a specific position being of a desired magnetic field strength in a vicinity of a front or rear end portion of the correcting portion,
the correcting portion is arranged such as to
cancel out the magnetic field generated by the magnet main body portion at a front or rear end portion of the magnet portion and
adjust a magnetic field gradient of a magnetic field generated by the magnet portion at the specific position by performing separation inwardly in a front/rear direc- tion from the front or rear end portion at which the correcting portion of the magnet main body portion is disposed in accordance with the magnetic field gradient of a magnetic field generated by the correcting portion, and the magnetic sensor is disposed at the specific position at which the magnetic field gradient is adjusted by the correcting portion.

2. The magnetic body detecting device according to claim 1, wherein the second correcting portion is shorter in front/rear length than the first correcting portion.

3. The magnetic body detecting device according to claim 1, wherein the first correcting portion is a permanent magnet of circular cylindrical shape with an inner diameter larger than an inner diameter of the magnet main body portion and the second correcting portion has a circular cylindrical shape with an inner diameter smaller than an inner diameter of the first correcting portion such that a hollow portion is formed in an interior of the correcting portion.

4. The magnetic body detecting device according to claim 1, wherein the desired magnetic field strength at the specific position is a magnetic field strength set based on a change amount of a detection value of the magnetic sensor accompanying a temperature change.

5. The magnetic body detecting device according to claim 1, wherein the magnetic sensor is disposed at the front end portion of the magnet portion and detects the magnetism of the magnetic body magnetized by the magnet portion.

6. The magnetic body detecting device according to claim 1, wherein the magnetic sensor is a geomagnetic sensor disposed at the rear end portion of the magnet portion and detects geomagnetism.

7. The magnetic body detecting device, wherein the correcting portion is constituted of
a first correcting portion disposed at an outer side in the front/rear direction with respect to the magnet main body portion and
a second correcting portion constituted of a permanent magnet disposed at an outer side in the front/rear direction with respect to the first correcting portion,
the first correcting portion adjusts a magnetic field gradient of the magnetic field generated by the magnet main body portion at the specific position by separating the magnet main body portion inwardly in the front/rear direction from the front or rear end portion of the magnet portion, and
the second correcting portion adjusts a magnetic field gradient at the specific position by canceling out a magnetic field at the front or rear end portion of the magnet portion generated by the magnet portion excluding the second correcting portion.

8. The magnetic body detecting device according to claim 7, wherein the specific position is formed by matching a peak of the magnetic field generated by the magnet portion excluding the second correcting portion and a peak of the magnetic field generated by the second correcting portion.

9. The magnetic body detecting device according to claim 7, wherein the specific position is a magnetic field null point of the desired magnetic field strength of substantially 0 and the magnetic field null point is formed by matching a peak, being of one of either a positive or negative sign, of the magnetic field generated by the magnet portion excluding the second correcting portion and a peak, being of the other of the positive or negative sign, of the magnetic field generated by the second correcting portion.

* * * * *